US012810429B1

(12) United States Patent
Khan et al.

(10) Patent No.: US 12,810,429 B1
(45) Date of Patent: Nov. 24, 2026

(54) SYSTEM AND METHOD FOR DEEP LEARNING OF IMPROVED BRAIN TUMOR DETECTION AND CLASSIFICATION

(71) Applicant: PRINCE MOHAMMAD BIN FAHD UNIVERSITY, Dhahran (SA)

(72) Inventors: Muhammad Attique Khan, Dhahran (SA); Faisal Yousif Al Anezi, Dhahran (SA)

(73) Assignee: PRINCE MOHAMMAD BIN FAHD UNIVERSITY, Dhahran (SA)

( * ) Notice: Subject to any disclaimer, the term of this patent is extended or adjusted under 35 U.S.C. 154(b) by 0 days.

(21) Appl. No.: 19/643,166

(22) Filed: Apr. 9, 2026

(51) Int. Cl.
*G06T 7/00* (2017.01)
*G16H 50/30* (2018.01)

(52) U.S. Cl.
CPC ........... *G06T 7/0012* (2013.01); *G16H 50/30* (2018.01); *G06T 2207/20081* (2013.01); *G06T 2207/20084* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS 10,223,610 B1 3/2019 Akselrod-Ballin et al.
2025/0238925 A1* 7/2025 Chan ...................... G06V 10/82

FOREIGN PATENT DOCUMENTS

CN 116863221 A 10/2023
CN 119206237 A 12/2024
CN 119541826 A * 2/2025 ........... G06T 7/0012
(Continued)

OTHER PUBLICATIONS

Chen W, Cai C, Tan X, Lv R, Zhang J, Du G. MAUNet: a mixed attention U-net with spatial multi-dimensional convolution and contextual feature calibration for 3D brain tumor segmentation in multimodal MRI. Front Neurosci. Oct. 8, 2025;19:1682603. (Year: 2025).*

(Continued)

*Primary Examiner* — David Ometz
(74) *Attorney, Agent, or Firm* — Oblon, McClelland, Maier & Neustadt, L.L.P.

(57) ABSTRACT

A system for analyzing brain medical images using a trained neural network. The system generates an initial feature representation from the medical image and applies spatial weighting masks corresponding to different anatomical brain regions to produce anatomically localized feature representations. Directional convolutional operations are applied to extract region-specific features and preserve tumor boundary edges. The region-specific features are processed at multiple spatial resolutions, and attention mechanisms are applied to weight features across the spatial resolutions. The resulting representations are combined using an attention-based fusion operation to generate a unified feature representation encoding spatial relationships between anatomical brain regions. Uncertainty associated with the unified feature representation is estimated via probabilistic feature weighting operation, and the unified feature representation is adjusted based on the determined uncertainty. A classification output indicating the likelihood of a brain tumor category is generated based on the adjusted unified feature representation.

20 Claims, 20 Drawing Sheets

(56) References Cited

FOREIGN PATENT DOCUMENTS

| | | | | | |
|---|---|---|---|---|---|
| CN | 120746999 | A | * | 10/2025 | ........... G06N 3/0464 |
| CN | 121306517 | A | * | 1/2026 | |
| CN | 121458740 | A | * | 2/2026 | ............... G06T 7/40 |
| WO | WO 00/65985 | | | 11/2000 | |
| WO | WO-2025046604 | A9 | * | 8/2025 | ............... G06T 7/11 |

OTHER PUBLICATIONS

Chaosheng Tang, et al., "HybridCANet:UNet-like network bridging CNN and attention for multimodal brain image segmentation", ICNCC '22: Proceedings of the 2022 11th International Conference on Networks, Communication and Computing, Dec. 2022, 7 Pages.

* cited by examiner

SYSTEM AND METHOD FOR DEEP LEARNING OF IMPROVED BRAIN TUMOR DETECTION AND CLASSIFICATION

BACKGROUND

Technical Field

The present disclosure is directed to a clinical application for brain tumor detection and classification using an uncertainty guided multi scale attention fusion network. More particularly, the present disclosure relates to a system and method for deep learning of improved brain tumor detection and classification.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The domain of automated brain tumor detection and classification primarily relied on a range of conventional image analysis techniques and deep learning based models, each presenting their own limitations and technical hurdles. Classical image processing techniques, including thresholding, region growing, watershed algorithms, and basic morphological operations, were widely used for tumor segmentation but often suffered from poor generalization, sensitivity to noise, and inadequate handling of the heterogeneous nature of brain tissues and tumors. Machine learning methods, such as support vector machines (SVMs), random forests, and k-nearest neighbors (KNN), were subsequently introduced, leveraging handcrafted texture, shape, and intensity-based features extracted from MRI or CT images. However, these hand-engineered feature approaches were inherently limited in their ability to capture high-level abstractions and complex nonlinear relationships, which are indispensable for the accurate delineation and classification of diverse tumor types and grades.

With the mainstream adoption of deep learning, convolutional neural networks (CNNs) emerged as the dominant architecture due to their powerful end-to-end feature extraction capabilities. Initial efforts utilized 2D CNNs that processed single MRI slices, but these methods failed to fully exploit the 3D contextual information inherent in volumetric brain data, adversely affecting segmentation performance and diagnostic reliability. Progressing to 3D CNNs enabled the capture of volumetric spatial dependencies, but at the expense of dramatically increased computational resource requirements, memory consumption, and training complexity. While transfer learning and hybrid models further improved performance by leveraging pre-trained feature extractors or integrating recurrent networks (e.g., LSTM, GRU) for temporal data, most conventional approaches, whether single-path or multi-path networks, treated the brain as a relatively homogeneous structure without explicit modeling of anatomical sub-regions such as cortical, subcortical, and ventricular areas. This deficiency often led to suboptimal tumor detection in clinically challenging cases where tumor boundaries were ill-defined, infiltrative, or overlapping with different anatomical compartments.

Another critical drawback in prevailing methods is the lack of robust mechanisms for uncertainty quantification and interpretability. Standard deep learning models provide deterministic predictions without accompanying confidence estimates, rendering them less suitable for critical clinical decision-making, wherein knowledge of prediction uncertainty is essential for risk management and case triage. Attempts to address this, such as Bayesian neural networks and Monte Carlo dropout, led to additional computational burdens and still struggled to produce trustworthy uncertainty maps aligned with anatomical contexts. Furthermore, attention mechanisms and pyramid feature hierarchies have been disclosed to improve focus on salient tumor regions and multi-scale structures. While these modules enhanced sensitivity to variable tumor morphology, they have generally not been guided by explicit anatomical knowledge or designed to integrate inter-region relationships, resulting in limited clinical interpretability and potentially redundant computations.

Existing solutions also suffer from instability and a lack of reproducibility across datasets with temporal or domain shifts, a common occurrence in clinical image acquisition protocols. Batch effects, scanner variability, and changes in input distributions frequently degrade the generalization performance of conventional models. Moreover, most commercial or research-based software tools involve cumbersome multi-stage workflows or require specialized post-processing and manual input, limiting their scalability and practical deployment in real-world settings.

Therefore, traditional and state-of-the-art technologies for automated brain tumor analysis face significant challenges: inadequate anatomical awareness, inability to assess or communicate uncertainty, inefficiency in handling tumors at different scales, limited cross-region feature integration, and insufficient robustness to temporal or domain variations. These technical barriers not only compromise diagnostic accuracy and operational efficiency but also hinder clinical adoption due to risks of misdiagnosis, increased manual workload, and lack of decision transparency.

SUMMARY

In some embodiments, a computer-implemented method for analyzing a medical image of a brain to detect a brain tumor using a trained neural network is described. The method includes generating an initial feature representation from the medical image using a neural network feature extractor comprising one or more convolutional layers. The method further includes applying a plurality of spatial weighting masks corresponding to different anatomical brain regions to the initial feature representation to generate a corresponding plurality of anatomically localized feature representations. The method further includes for each anatomically localized feature representation, extracting anatomical region-specific features using directional convolutional operations having different kernel orientations and combining the extracted features with features generated by convolutional operations configured to preserve edge discontinuities associated with tumor boundaries. The method further includes for each anatomically localized feature representation, processing the region-specific features at multiple spatial resolutions corresponding to different portions of the medical image and applying an attention mechanism that weights features extracted at the different spatial resolutions to generate a scale-weighted region-specific feature representation associated with spatial structures in the medical image. The method further includes applying an attention-based fusion operation to jointly process the scale-weighted region-specific feature representations corresponding to different anatomical brain regions depicted in the medical image, thereby generating a unified feature representation encoding spatial relationships between the anatomical brain regions. The method further includes computing attention weights for the unified feature representation using a probabilistic feature weighting operation that estimates uncertainty associated with the unified feature representation and applies the estimated uncertainty to modulate the unified feature representation. The method finally includes generating, based on the uncertainty modulated unified feature representation, a classification output indicating a likelihood of a brain tumor category.

In some embodiments, processing the input skin lesion image to generate the refined feature representations includes combining outputs of a plurality of convolutional operations within at least one of the convolutional stages using channel-wise concatenation to form the refined feature representations.

In some embodiments, the plurality of spatial weighting masks includes learnable parameters jointly optimized with parameters of the neural network, and no externally generated anatomical segmentation is used to define the spatial weighting masks.

In some embodiments, processing the anatomical region-specific features at multiple spatial resolutions includes down-sampling the anatomical region-specific features to a plurality of reduced spatial resolutions, applying convolutional operations at each reduced spatial resolution, and up-sampling outputs of the convolutional operations to a common spatial resolution prior to applying the attention mechanism.

In some embodiments, the attention-based fusion operation includes applying a self-attention mechanism across the anatomically localized feature representations to generate a fused feature representation encoding interactions between different anatomical brain regions at corresponding spatial locations.

In some embodiments, training the neural network, the training comprises generating stochastic attention weights in the probabilistic feature weighting operation by estimating an uncertainty value for feature channels, and injecting noise scaled by the estimated uncertainty value prior to computing attention weights.

In some embodiments, training the neural network, the training comprises processing, by a temporal consistency module, the unified feature representation and an augmented feature representation to generate corresponding consistency-constrained feature representations, wherein the augmented feature representation is generated by applying a spatial augmentation to the unified feature representation, and updating parameters of the neural network based on differences between the consistency constrained feature representations.

In some embodiments, updating parameters of the neural network includes optimizing a composite loss function including a classification loss based on the classification output, an anatomical consistency loss based on spatial differences between the plurality of spatial weighting masks, an uncertainty regularization loss based on uncertainty values associated with feature channels, a cross-scale coherence loss based on differences between feature representations at different spatial resolutions, and a temporal consistency loss based on differences between the unified feature representation and the augmented feature representation.

In some embodiments, during an inference phase, the spatial augmentation and generation of the augmented feature representation are disabled.

In some embodiments, the temporal consistency module comprises applying an instance of the probabilistic feature weighting operation to the augmented feature representation prior to generating the consistency constrained feature representations.

In some embodiments, the directional convolutional operations include convolutional kernels oriented along at least two different angular directions to capture orientation-specific feature patterns within the anatomical brain regions.

In some embodiments, the attention mechanism that weights features extracted at the different spatial resolutions computes normalized weighting coefficients across the multiple spatial resolutions prior to generating the scale-weighted region-specific feature representation.

In another exemplary embodiment, a system for analyzing a medical image of a brain is described. The system includes one or more processors and a memory storing instructions that, when executed by the one or more processors, cause the one or more processors to generate an initial feature representation from the medical image using a neural network feature extractor. The system further includes applying a plurality of spatial weighting masks corresponding to different anatomical brain regions to the initial feature representation to generate a plurality of anatomically localized feature representations. The system further includes applying directional convolutional operations to the anatomically localized feature representations to generate anatomical region-specific features. The system further includes applying attention mechanisms to the anatomical region-specific features to weight features across multiple spatial resolutions and across the anatomical brain regions, thereby generating a unified feature representation encoding spatial relationships between the anatomical brain regions. The system further includes determining uncertainty associated with the unified feature representation and adjusting the unified feature representation based on the determined uncertainty. The system finally includes generating, based on the adjusted unified feature representation, an output indicating a likelihood of a brain tumor category.

In some embodiments, the plurality of spatial weighting masks includes learnable parameters jointly optimized with parameters of the neural network, and no externally generated anatomical segmentation is used to define the spatial weighting masks.

In some embodiments, the one or more processors are further configured to process the anatomical region-specific features at multiple spatial resolutions by down-sampling the anatomical region-specific features to a plurality of reduced spatial resolutions, applying convolutional operations at each reduced spatial resolution, and up-sampling outputs of the convolutional operations to a common spatial resolution prior to applying the attention mechanisms.

In some embodiments, the attention mechanisms include a self-attention mechanism applied across the anatomically localized feature representations to generate a fused feature representation encoding interactions between different anatomical brain regions at corresponding spatial locations.

In some embodiments, the memory further stores instructions that, when executed by the one or more processors during training of the neural network, cause the one or more processors to generate stochastic attention weights by determining an uncertainty value for feature channels and injecting noise scaled by the determined uncertainty value prior to adjusting the unified feature representation.

In some embodiments, the memory further stores instructions that, when executed by the one or more processors during training of the neural network, cause the one or more processors to apply a spatial augmentation to the unified feature representation to generate an augmented feature representation apply an instance of the probabilistic feature weighting operation to the augmented feature representation and update parameters of the neural network based on differences between the unified feature representation and the augmented feature representation.

In another exemplary embodiment, a non-transitory computer-readable medium storing instructions executed by one or more processors is described. The execution of instructions by the one or more processors includes generating an initial feature representation from a medical image of a brain using a neural network feature extractor. The execution of instructions by the one or more processors further includes applying a plurality of spatial weighting masks corresponding to different anatomical brain regions to the initial feature representation to generate a plurality of anatomically localized feature representations. The execution of instructions by the one or more processors further includes applying directional convolutional operations to the anatomically localized feature representations to generate anatomical region-specific features. The execution of instructions by the one or more processors further includes applying attention mechanisms to the anatomical region-specific features to weight features across multiple spatial resolutions and across the anatomical brain regions, thereby generating a unified feature representation encoding spatial relationships between the anatomical brain regions. The execution of instructions by the one or more processors further includes determining uncertainty associated with the unified feature representation and adjust the unified feature representation based on the determined uncertainty. The execution of instructions by the one or more processors finally includes generating, based on the adjusted unified feature representation, an output indicating a likelihood of a brain tumor category In some embodiments, the instructions further cause the one or more processors, during training of the neural network, to generate stochastic attention weights by estimating an uncertainty value for feature channels and injecting noise scaled by the estimated uncertainty value prior to adjusting the unified feature representation In some embodiments, the instructions further cause the one or more processors, during training of the neural network, to apply a spatial augmentation to the unified feature representation to generate an augmented feature representation, apply an instance of the probabilistic feature weighting operation to the augmented feature representation and update parameters of the neural network based on differences between the unified feature representation and the augmented feature representation.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
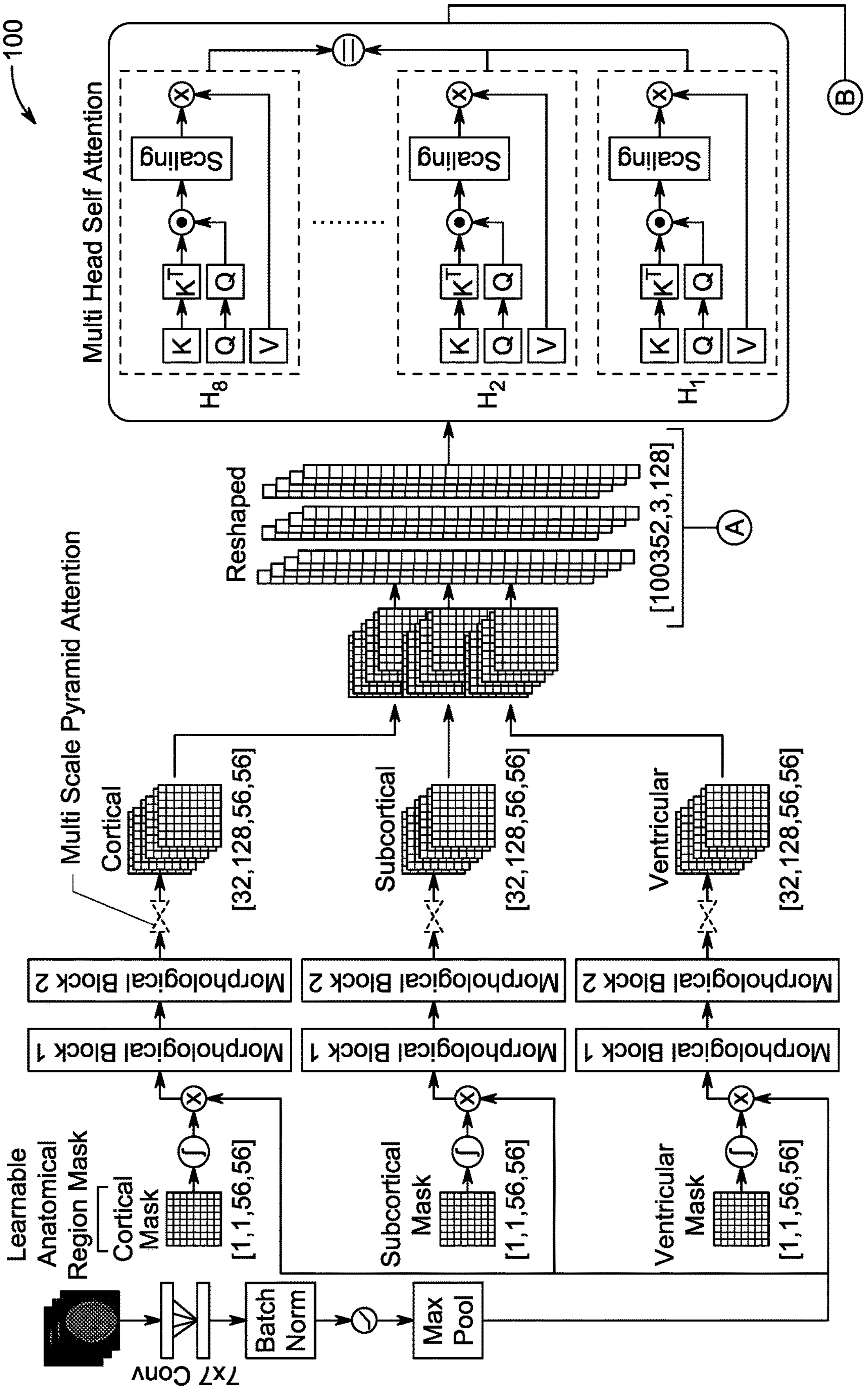
FIG. 1 depicts a block diagram of a Multi-Scale Attention Fusion Network with Anatomical Prior Learning (MAFN-APL) architecture for brain tumor classification, according to certain embodiments.
Figure 1:
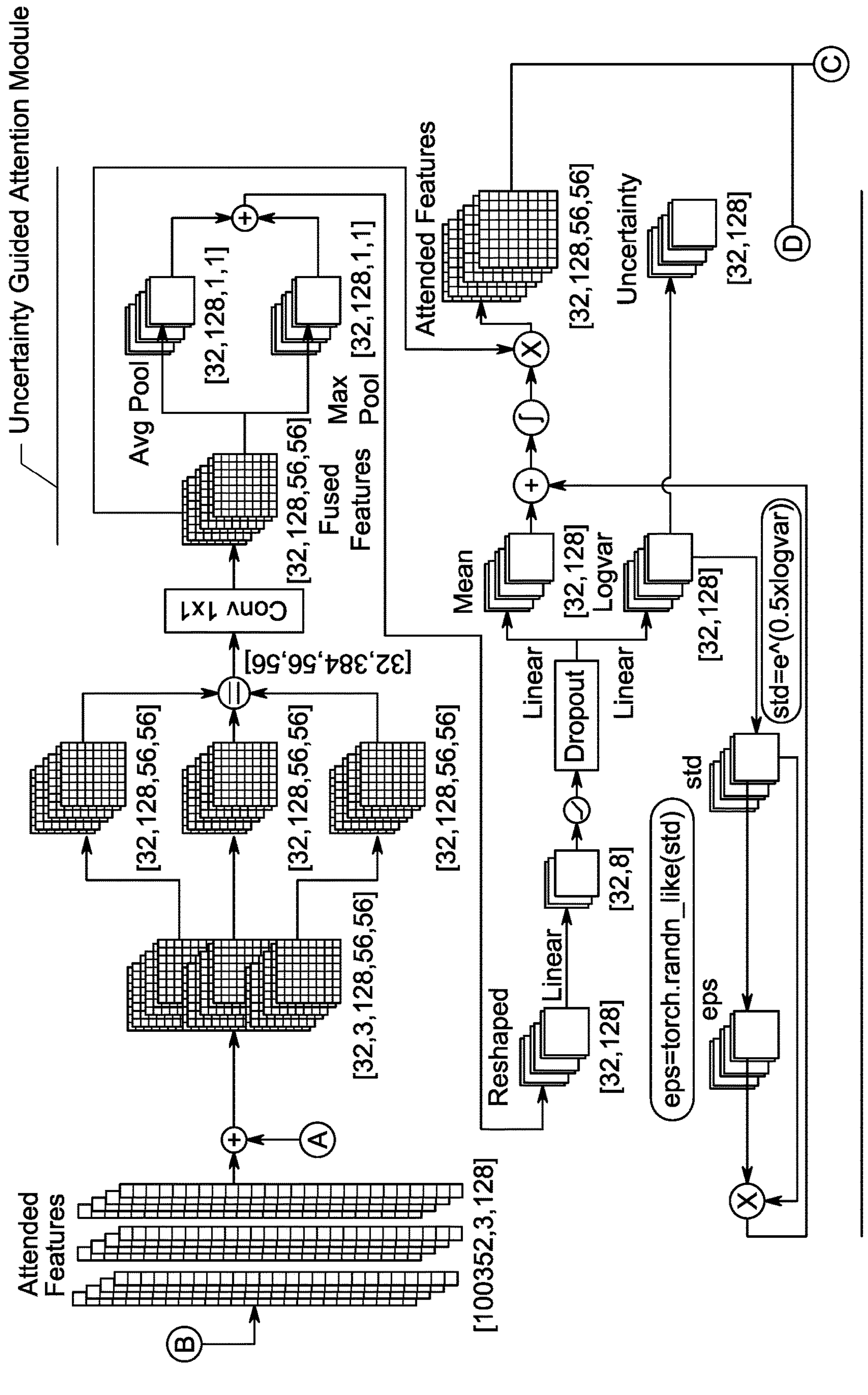
Figure 1:
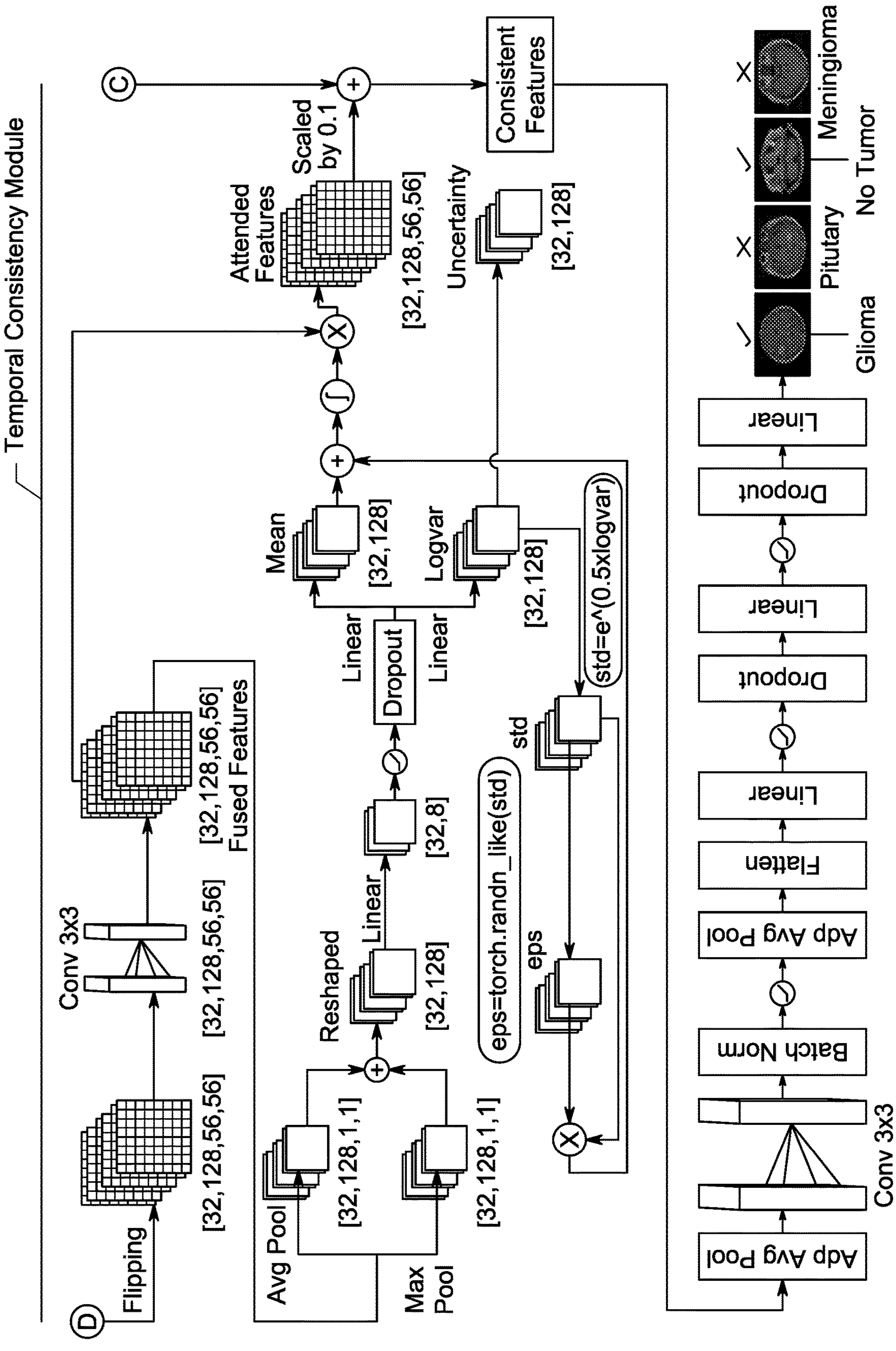

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

The field of automated brain tumor detection and classification has historically progressed through several distinct technological generations, each characterized by its own methodologies, underlying assumptions, and technical limitations. Early research in this area was predominantly centered around classic image analysis techniques, including but not limited to thresholding algorithms, region growing strategies, watershed transformation, and fundamental morphological operations. These approaches were primarily applied to neuroimaging modalities such as magnetic resonance imaging (MRI) and computed tomography (CT) scans in an effort to distinguish tumor tissues from healthy brain structures. Despite their simplicity and computational efficiency, these conventional algorithms frequently demonstrated significant limitations, particularly their inability to robustly generalize across patient populations and imaging protocols. The major challenges included high sensitivity to noise and changes in intensity distributions due to scanner variability, and limited capability to effectively segment tumors with heterogeneous shapes, variable textures, or infiltrative boundaries that blend with surrounding normal brain tissue. In addition, these algorithms often required manual parameter tuning and were unable to automatically adapt to the wide spectrum of tumor manifestations encountered in clinical practice.

To overcome the inherent rigidity of handcrafted rules, the domain gradually embraced machine learning methods such as support vector machines (SVMs), random forests, decision trees, and k-nearest neighbor (KNN) classifiers. These algorithms were typically powered by expert-designed features, including texture descriptors (e.g., Gabor filters, local binary patterns), intensity histograms, statistical moments, and shape characteristics derived from predefined tumor regions. Though these feature-driven approaches improved the adaptability of models to various tumor attributes, they remained fundamentally constrained by the quality and completeness of the manually selected features. Hand-engineered representations struggled to capture highly abstract or non-linear relationships present in complex brain anatomy and pathology, thus limiting performance, especially for challenging cases such as multifocal tumors, those with diffuse margins, or atypical contrast enhancement patterns.

With the rapid evolution of artificial intelligence, deep learning—particularly convolutional neural networks (CNNs)—emerged as the prevailing paradigm for medical image analysis. Early implementations typically used 2D CNNs, which extracted features from individual axial, coronal, or sagittal slices. Although 2D CNNs offered remarkable improvements in terms of automation and consistency, they failed to leverage the volumetric and spatial continuity inherent to 3D neuroimaging data. This oversight often led to incomplete feature representation and reduced sensitivity in segmenting tumors that span multiple slices or exhibit subtle 3D morphology. The introduction of 3D CNNs marked a significant technological advancement, enabling the network to simultaneously process contiguous image volumes and capture contextual dependencies across all three anatomical planes. However, such models imposed substantial computational overhead, demanding large memory resources and longer training times, and were more susceptible to overfitting due to increased parameter space and limited annotated volumetric datasets.

Multiple strategies emerged in an attempt to address the aforementioned shortcomings. Transfer learning was widely employed to mitigate data scarcity issues by fine-tuning pre-trained models from large generic image datasets to the medical domain. Hybrid architectures, integrating convolutional schemes with recurrent neural networks such as long short-term memory (LSTM) or gated recurrent units (GRUs), allowed some consideration of sequential or temporal information in dynamic image sequences. Still, many conventional and even advanced deep models approached the brain as a largely homogeneous tissue construct, neglecting the complex anatomical subdivisions—such as cortical, subcortical, and ventricular regions—that can exhibit different tumor invasion patterns. This lack of structural awareness often resulted in compromised accuracy for tumors that cross, infiltrate, or co-localize with specific neuroanatomical regions, making the detection and delineation particularly challenging in clinically ambiguous or overlapping scenarios.

Another vital technological gap present in existing methods pertains to uncertainty quantification and model interpretability, both of which are critical for high-stakes clinical decision-making. Conventional deep learning networks generally yield deterministic outputs, offering no mechanisms for expressing the model's confidence in its predictions—a significant drawback when dealing with subtle or borderline tumor cases where diagnostic ambiguity is inherently high. Bayesian neural networks, ensembles, and Monte Carlo (MC) dropout have been disclosed as solutions, providing probabilistic predictions and uncertainty estimates. Despite these developments, their practical adoption has been hampered by considerable increases in computation and memory requirements, and empirical results often fell short in generating anatomically meaningful uncertainty estimates compatible with clinicians' expectations. Furthermore, advanced network modules such as attention mechanisms and feature pyramid networks were designed to enhance model focus on salient tumor areas and integrate information across multiple spatial scales. Although these architectural enhancements improved responsiveness to variable tumor size and morphology, they generally lacked anatomical guidance or explicit region-to-region interaction modeling, thus limiting their interpretability and leaving potentially useful domain knowledge underexploited.

Additionally, a persistent challenge in automated brain tumor analysis is the reproducibility and robustness of disclosed solutions across real-world clinical environments. Significant variability emerges from temporal, scanner, or protocol differences encountered in diverse hospital settings ("domain shift" and "batch effects"), often substantially diminishing a model's generalization capability beyond its training cohort. Furthermore, most available commercial and research tools require complex multi-stage pre- and post-processing pipelines, combined with significant manual intervention for initialization, error correction, or fine delineation. Such requirements materially hinder the workflow efficiency and scalability necessary for broad clinical implementation.

Therefore, the landscape of conventional and state-of-the-art systems developed for automated brain tumor detection, segmentation, and classification is characterized by a series of interrelated technical challenges: (1) Insufficient encoding of detailed neuroanatomical context, leading to incomplete modeling of tumor interactions with specific brain regions; (2) absence of reliable uncertainty assessment capabilities, which impacts the trust placed in automated outputs for diagnostic and treatment planning purposes; (3) inefficiency in handling tumors of diverse scales or appearance, especially for multifocal or infiltrative lesions; (4) limited mechanisms for aggregating and contextualizing inter-regional features crucial for understanding biological and clinical implications; and (5) inadequate robustness and reproducibility under the real-world variations encountered in clinical image acquisition and operational protocols. Collectively, these challenges not only undermine the diagnostic and operational value of existing automated solutions but also restrict their real-world clinical impact by perpetuating risks of misdiagnosis, increased dependency on time-consuming manual procedures, and reduced transparency in algorithmic decision-making.

Disclosed are embodiments of a brain tumor detection system for analyzing medical images of a brain using a neural network that is structured to process image features in an anatomically informed and uncertainty-aware manner. Instead of processing the image as a whole, the system first separates the image into different anatomical brain regions using spatial weighting masks and extracts features specific to each region, including features that preserve tumor edges. The system includes an anatomical region decomposer that enables region-specific feature extraction by segmenting the brain into various anatomical regions, such as cortical, subcortical, and ventricular regions, ensuring anatomically informed learning. It then analyzes these features at multiple scales and combines information across regions using attention mechanisms to capture relationships within the brain. For example, the system includes (a) a multi-scale pyramid attention module that captures tumor features at various scales, effectively handling variations in tumor shape and size, and (b) a cross-region attention fusion module that allows interaction among region-specific features to generate a unified representation, improving classification precision. The system includes an uncertainty-guided attention module that determines how uncertain different features are and adjusts them accordingly, improving reliability. During training, a temporal consistency module further enhances robustness by introducing controlled randomness based on uncertainty and by enforcing consistency between original and augmented representations. Together, these elements enable more accurate and stable identification of brain tumor categories compared to conventional approaches.

Referring now to FIG. 1, a Multi-Scale Attention Fusion Network with Anatomical Prior Learning (MAFN-APL) architecture for brain tumor classification is disclosed, according to certain embodiments.

In some embodiments, the brain tumor detection system is implemented using a neural network model, such as the MAFN-APL model 100, and FIG. 1 illustrates the architecture of such a neural network model. In an embodiment, the disclosed architecture comprises both hardware and software components working collaboratively to achieve precise and informative analysis results. Central to the disclosed architecture are one or more processors, such as central processing units (CPUs), graphics processing units (GPUs), or specialized neural network accelerators, which provide the requisite computational power for intensive image processing tasks. Accompanying these processors is a memory structure, typically encompassing both volatile memory (RAM) for temporary processing and non-volatile memory for instruction and model storage. The memory holds computer-readable instructions, often as part of a pre-trained deep learning framework, which, when executed by the processors, coordinate the entire analytical pipeline.

Upon execution, a first functional stage involves generating an initial feature representation from the input medical brain image. This is accomplished using a neural network feature extractor, such as a convolutional neural network (CNN) or a vision transformer (ViT), which processes the input data at multiple levels of abstraction. The extractor produces a set of latent features that capture relevant visual patterns and characteristics in medical images, such as tissue textures, intensity variations, and structural delineations.

Subsequently, these initial features are decomposed spatially using a plurality of spatial weighting masks. Each spatial weighting mask is designed to correspond to a distinct brain region (e.g., lobes, cortical, subcortical, ventricles, basal ganglia), enabling region-specific analysis. By selecting features with these masks, the system generates a plurality of anatomically localized feature representations, where each representation contains information primarily from a specific anatomical region, thus improving the localization and interpretability of subsequent feature processing.

Once anatomically localized feature representations are obtained, the system applies directional convolutional operations. These operations use tailored convolutional filters aligned with specific spatial directions (e.g., axial, sagittal, coronal), allowing the extraction of features that align with the orientation of anatomical structures. This results in the generation of anatomical-region-specific features that are sensitive to both location and directional context within each anatomical domain, thereby enhancing the model's ability to detect region-dependent anomalies or patterns.

Attention mechanisms are then introduced to further refine feature analysis. These mechanisms operate both within and across anatomical regions, weighing the relative importance of features at multiple spatial resolutions as well as across different anatomical partitions. Through this, the system produces a unified feature representation, a high-dimensional vector or tensor that encodes not only the detailed information from individual regions but also the spatial relationships and interactions between these regions. This unified feature representation is crucial for capturing the brain's holistic context as visualized in the medical image.

To further strengthen the robustness of the analysis, the system determines an uncertainty measure for the unified feature representation. This may involve Bayesian or ensemble techniques to quantify prediction confidence or epistemic/aleatoric uncertainty. The system then adaptively adjusts the unified feature representation based on this uncertainty information, such as by attenuating features with high associated uncertainty or reweighting the representation to focus on more confidently predicted features.

Finally, the adjusted unified feature representation is provided as input to the system's classification or prediction head. Here, a decision module, often a fully connected neural network layer or a probabilistic model, generates an output. This output indicates a likelihood score or probability reflecting the categorization of a potential brain tumour, with specific output categories (such as glioblastoma, meningioma, metastasis, or non-tumorous tissue) 1 and possibly corresponding confidence levels or auxiliary diagnostic information. Thus, the disclosed architecture 100 tightly integrates advanced machine learning, anatomical priors, and uncertainty quantification to deliver highly detailed and clinically meaningful analysis of brain medical images.

The disclosed architecture of the MAFN-APL model 100 comprises following elements, components, or modules: anatomical region decomposer, morphological block, a multi-scale pyramid attention block, a cross-region attention fusion module, uncertainty-guided attention module and a temporal consistency module.

Figure 2:
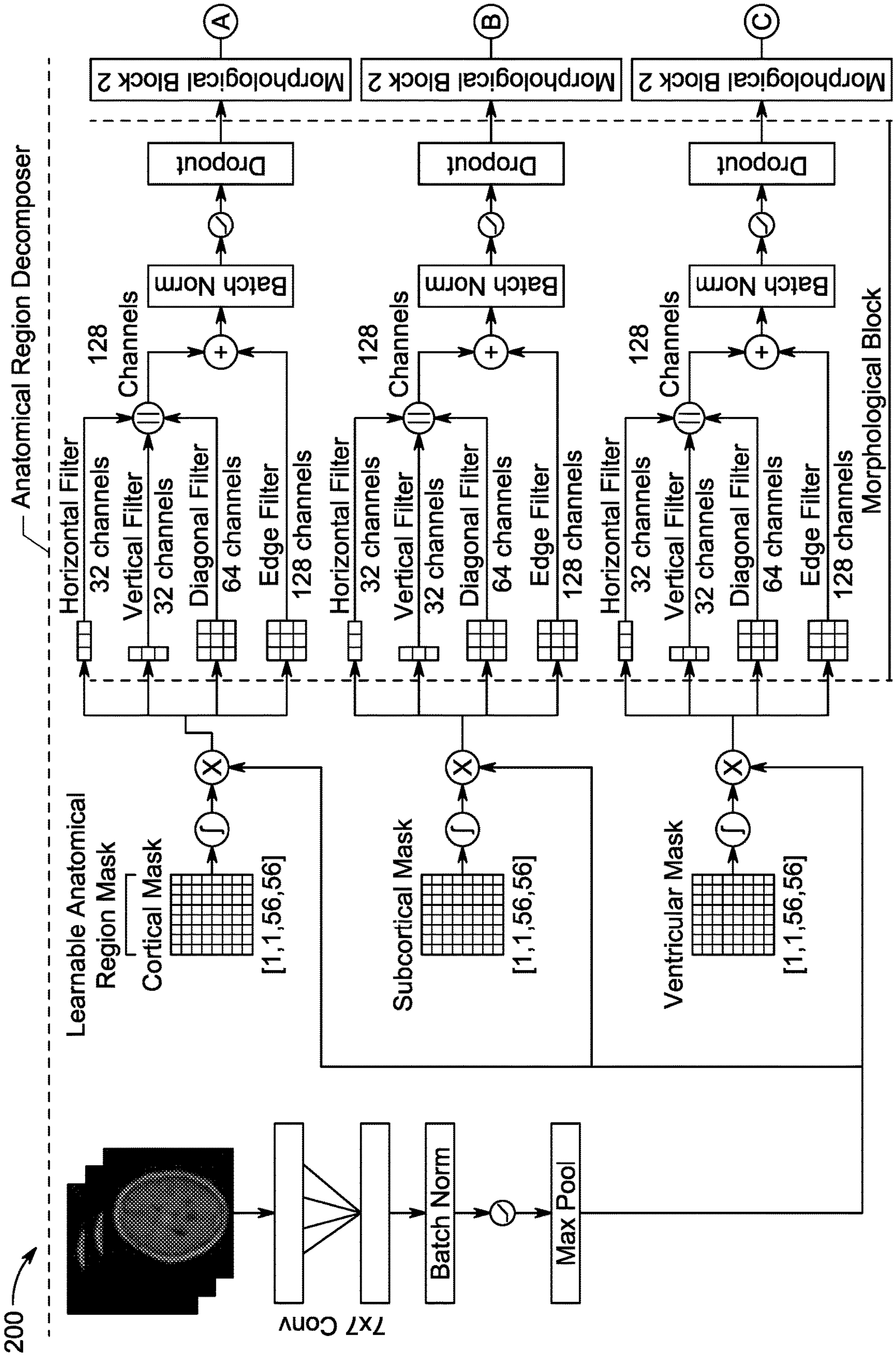
FIG. 2 depicts a block diagram of an Anatomical Region Decomposer, which consists of two morphological blocks and a multi-scale pyramid attention block for each anatomical region, according to certain embodiments.
Figure 2:
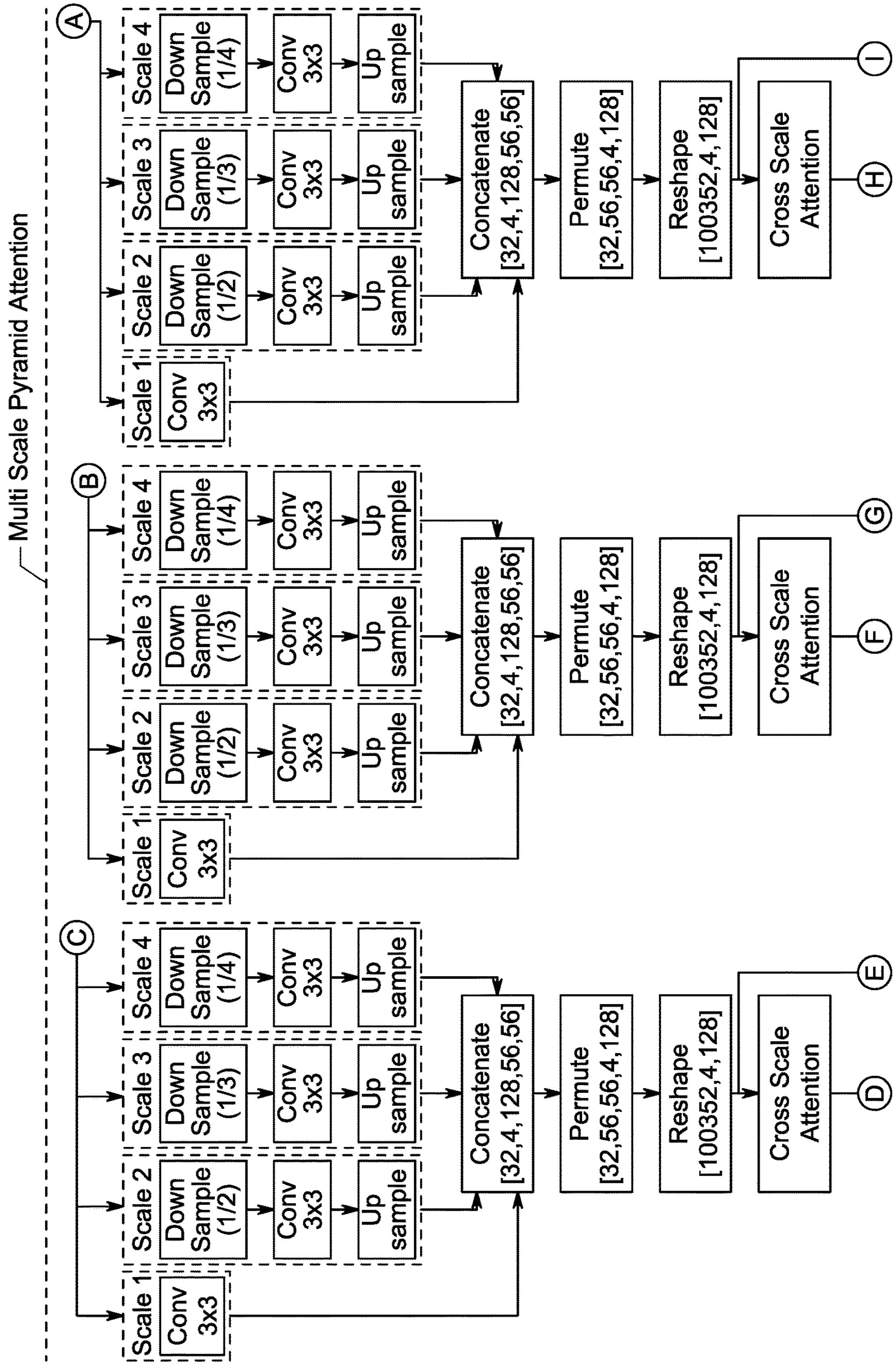
Figure 2:
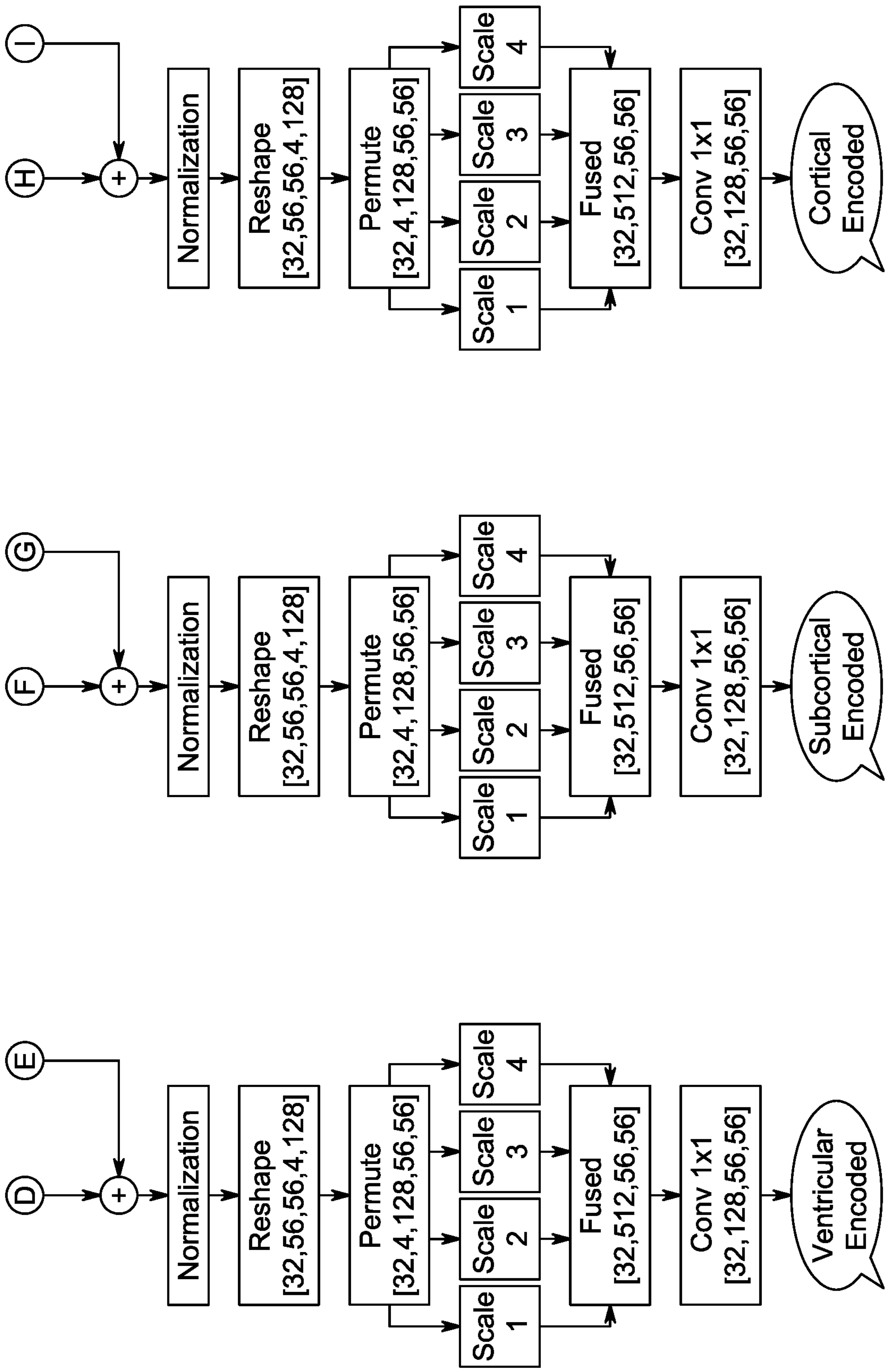

A pictorial representation of the disclosed anatomical region block is shown in FIG. 2. Referring now to FIG. 2, the anatomical region decomposer consists of multiple morphological blocks (e.g., two morphological blocks) and a multi-scale pyramid attention block for each anatomical region, according to certain embodiments.

In some embodiments, brain tumors appear and behave differently depending on the region of the brain in which they are present. Having prior knowledge of the brain's anatomical regions is very helpful in classifying tumor types. For this purpose, an anatomical region decomposer is disclosed that decomposes a human brain into multiple (e.g., three) anatomical regions such as cortical, subcortical, and ventricular, to support region-specific feature extraction. The anatomical region decomposer takes a medical image of the brain (e.g., MRI image of the human brain) as input and passes it through a convolutional layer (e.g., a 7×7 convolutional layer) for initial feature extraction. It may be followed by a batch normalization layer to normalize the input and a GELU activation layer to introduce non-linearity.

After that, a max pooling layer is applied, downsampling the original image size (e.g., from 224×224×3 to 56×56×3, where 56×56 represents the spatial dimensions and 3 represents the number of channels). Mathematically, it can be represented as:

$$F_i = \oint(\varrho(\phi((W_i * X) + b_i))) \tag{1}$$

where X is the input image, $W_i$ and $b_i$ represent the weights and bias term for the initial convolutional layer, * represents a convolutional operation, $\phi$ stands for batch normalization, $\varrho$ denotes GELU activation, $\oint$ represents Max Pooling, and $F_i$ represents the initially extracted feature map.

Three learnable anatomical region masks of a specified size (e.g., [1,1,56,56]) are initialized with random weights and later optimized to map the respective anatomical region. A sigmoid activation function is applied to these masks to highlight the region of interest. The resulting weight tensors are multiplied element-wise with the initially extracted feature map to produce region-specific feature maps. Let $$M_c, M_s, M_v \in \mathbb{R}^{1\times 1\times \frac{H}{4}\times \frac{W}{4}}$$

represent the cortical, subcortical, and ventricular region masks. Then, the generation of region-specific feature maps can be represented as:

$$F_c = F_i \otimes \psi(M_c) \tag{2}$$

$$F_s = F_i \otimes \psi(M_s) \tag{3}$$

$$F_v = F_i \otimes \psi(M_v). \tag{4}$$

Here, $\psi$ represents sigmoid activation, $\otimes$ represents element-wise multiplication, and $F_c$, $F_s$, and $F_v$ represent cortical, subcortical, and ventricular feature maps, respectively. These feature maps are then passed to their respective encoders where each encoder consists of two morphological blocks and a multi-scale pyramid attention block.

The morphological blocks are designed to mimic tumor spread by utilizing customized directional and edge-preserving convolutional kernels to capture respective features. The motivation behind this is the fact that brain tumors often spread along a certain axis, such as along the white matter tract or near anatomical boundaries. By utilizing these morphological blocks, the system is enabled to capture sophisticated morphological variations that are crucial to classify tumor types. The first morphological block takes a region-specific feature map as an input and applies a directional convolutional kernel (e.g., a 1×3, 3×1, and a 3×3 convolutional kernel) to capture horizontal, vertical, and diagonal features, respectively.

Let $$F_j \in \mathbb{R}^{B\times C\times \frac{H}{4}\times \frac{W}{4}}$$

is the region-specific feature map, where j∈c, s, v. The directional feature maps are generated as:

$$F_{hl} = W_{1\times 3} * F_j + b_{hl} \tag{5}$$

$$F_{vl} = W_{3\times 1} * F_j + b_{vl} \tag{6}$$

$$F_{dl} = W_{3\times 3} * F_j + b_{dl} \tag{7}$$

where $F_{hl}$, $F_{vl}$ and $F_{dl}$ represent horizontal, vertical, and diagonal feature maps, respectively. Another 3×3 kernel is applied to a feature map for edge preservation, ensuring that critical details about tumor boundaries remain preserved. Mathematically, it can be represented as:

$$F_E = W_{3\times 3} * F_j + b_E \tag{8}$$

Three directional feature maps (horizontal, vertical, and diagonal) are concatenated to generate a combined representation of directional features which are then combined with edge preserving features by a residual connection.

$$F_{dir} = F_{hl} \| F_{vl} \| F_{dl} \tag{9}$$

$$F_{com} = F_{dir} + F_E \tag{10}$$

where || represents concatenation, $F_{dir}$ represents combined representation of directional features, $F_E$ represents edge preserving features, and $F_{com}$ represents the combined region-specific feature representation.

This is followed by batch normalization to stabilize the training process, GELU activation to capture complex patterns, and a dropout layer to prevent overfitting. Mathematically:

$$F_{mor1} = \wp(\varrho(\phi(F_{com}))). \tag{11}$$

Here, $\wp$ represents a dropout layer and $F_{mor1}$ represents the output of the first morphological block. After that, another morphological block is incorporated to refine the feature representation, and the output of the second morphological block is passed to the multi-scale pyramid attention block.

In some embodiments, brain tumors can vary in shape and size, and they may appear differently in different scales. This characteristic of brain tumors is addressed by a multi-scale pyramid attention block that processes the feature maps at different scales to capture both fine-grained and global features. A multi-scale pyramid attention block takes the output of the second morphological block as input and processes it at four different scales. At the first scale, the spatial dimensions of the input feature map [56×56] remain the same and a 3×3 convolutional layer is applied to extract information. At scale 2, the spatial dimensions are down sampled to [28×28], and a 3×3 convolutional layer is applied to the reduced feature map to extract scale-specific information. After a convolutional layer, the feature map is up-sampled to [56×56]. At scale 3, spatial dimensions are down-sampled to [14×14], and at scale 4, they are down-sampled to [7×7] before applying a convolutional layer.

After extracting information, the feature maps are again sampled to [56×56]. Mathematically, it can be represented as:

$$F_1 = W_{3x3} * F_{mor2} + b_1 \tag{12}$$

$$F_k = U(W_{3x3} * \cap(F_{mor2}) + b_k) \because k = 2, 3, 4. \tag{13}$$

Here, $F_{mor2}$ represents the output of the second morphological block, ∩ represents down sampling, and U represents up-sampling.

The outputs of these four scales are then stacked, permuted, reshaped, and passed to a cross-scale attention block, where the importance of features at each scale is weighted to enable the model to focus on the most relevant scale for each tumor. These attended features are then combined with the reshaped original features via residual connection and passed to a normalization layer, which can be represented as:

$$F_{stacked} = F_1 \| F_2 \| F_3 \| F_4 \tag{14}$$

$$F_{stacked}^{B\times 4\times C\times\frac{H}{4}\times\frac{W}{4}} \rightarrow F_{permuted}^{B\times\frac{H}{4}\times\frac{W}{4}\times 4\times C} \rightarrow F_{reshaped}^{B*\frac{H}{4}*\frac{W}{4}\times 4\times C}. \tag{15}$$

This reshaped feature map is used to compute key, query, and value metrices for multi-head self-attention in a cross-scale attention block.

Let $$W_q, W_k, W_v \in \mathbb{R}^{C\times d},$$

where $$d = \frac{c}{N_h}$$

and $$F^* = F_{reshaped}^{B*\frac{H}{4}*\frac{W}{4}\times 4\times C}.$$

Here, $N_h$=8 and represents the number of heads. For the given stacked feature map, the output of the cross-scale attention block is computed as:

$$F_A = ∰\left(\sqsubseteq\left(\left\{\delta\left(\frac{(F^* W_q^h)(F^* W_k^h)^T}{\sqrt{d}}\right)(F^* W_v^h)\right\}_{h=1}^{N_h}\right)W_o + F^*\right). \tag{16}$$

Here, ∰ represents normalization layer, ⊑ represents concatenation, δ represents SoftMax activation, and $W_o$ represents projection layer. This equation represents how the outputs of each head in multi-head self-attention are concatenated with each other and after adding with the original reshaped tensor are passed to the normalization layer.

This normalized tensor is then again reshaped, permuted, and projected into 4 individual feature maps where each feature map is the attended version of the original feature map.

$$F_{normalized}^{B*\frac{H}{4}*\frac{W}{4}\times 4\times C} \rightarrow F_{reshaped}^{B\times\frac{H}{4}\times\frac{W}{4}\times 4\times C} \rightarrow F_{permuted}^{B\times 4\times C\times\frac{H}{4}\times\frac{W}{4}} \tag{17}$$

$$F_{permuted}^{B\times 4\times C\times\frac{H}{4}\times\frac{W}{4}} \twoheadrightarrow F_k^{B\times C\times\frac{H}{4}\times\frac{W}{4}} \because k = 1, 2, 3, 4 \tag{18}$$

These four feature maps are then fused and passed to the 1×1 convolutional layer to generate the final representation of region-specific feature map.

$$F_j^i = W_{1\times 1} * \ddagger\left(F_k^{B\times C\times\frac{H}{4}\times\frac{W}{4}}\right) + b_j' \tag{19}$$

Here, ‡represents a fusion operation and $$F_j'$$

represents a final anatomical region-specific feature representation, where j∈c, s, v for cortical, subcortical, and ventricular regions, respectively.

Figure 3:
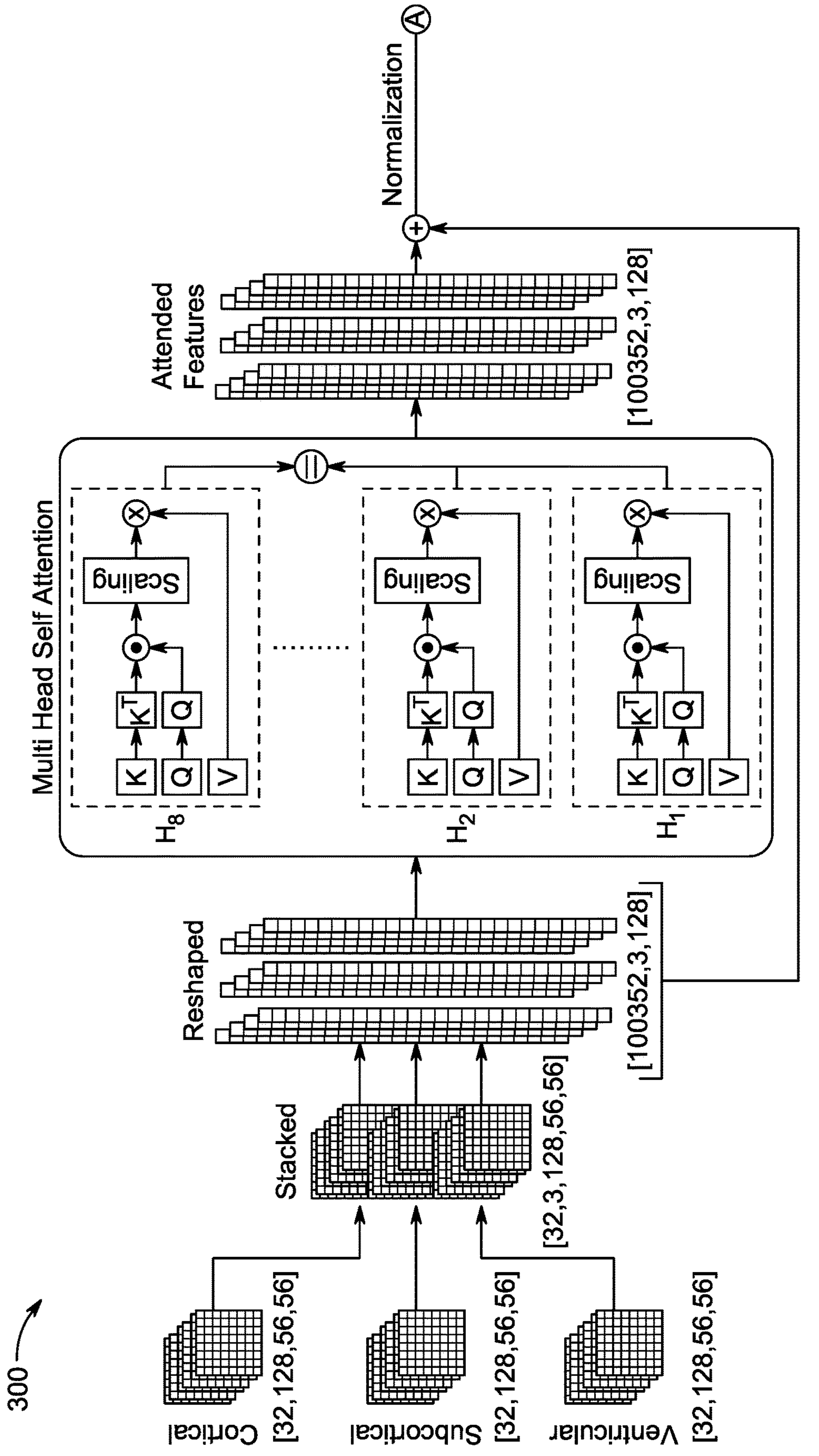
FIG. 3 depicts a block diagram of a cross-region attention fusion module for region-specific feature integration, according to certain embodiments.
Figure 3:
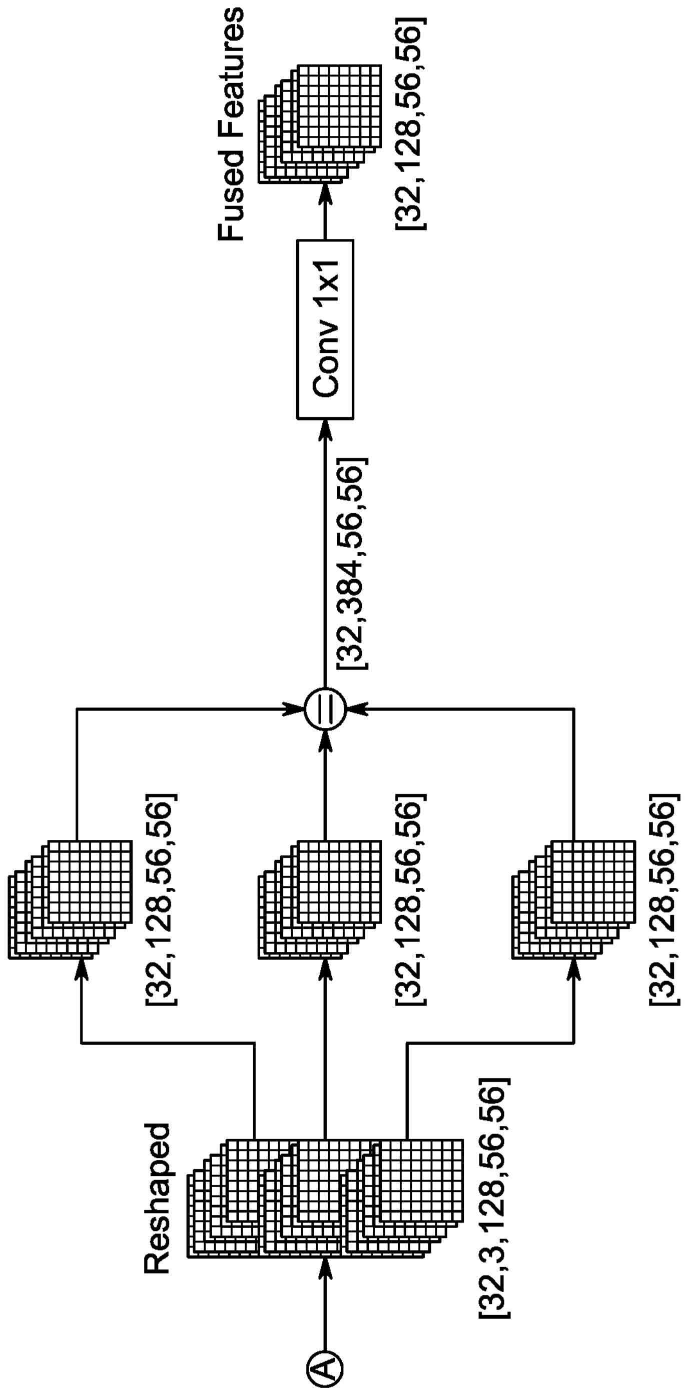

FIG. 3 depicts a block diagram of a cross-region attention fusion module for region-specific feature integration, according to certain embodiments. In some embodiments, brain tumors often span over more than one anatomical region or exhibit characteristics that demonstrate inter-regional dependencies. To address this, a cross-region attention fusion module is designed that enables the system to understand how one anatomical region influences other regions by integrating region-specific feature maps into a single, combined representation for enhanced tumor classification. The disclosed module takes feature maps of multiple anatomical brain regions (e.g., three anatomically localized feature maps) generated by the anatomical region decomposer as input and stacks them together along a new dimension. These stacked feature maps are then permuted and reshaped before being entered into the multi-head self-attention module, where multiple heads (e.g., eight heads) process the feature maps to model the interactions between the regions. The self-attention module computes similarities between regions for each spatial location to generate attention weights for each feature map. These attended features are then combined with the original reshaped features via a residual connection before passing through the normalization layer. The normalized features are then reshaped, permuted, and projected back into three individual feature maps, which are subsequently fused and passed through a fusion layer to generate a unified, enhanced feature representation.

Let $$F_c', F_s', F_v' \in \mathbb{R}^{B\times C\times\frac{H}{4}\times\frac{W}{4}}$$

be the region specific feature maps generated by the anatomical region decomposer module; hence, the mathematical representation of the region attention fusion module is as follows:

$$F'_{stacked} = F'_c \| F'_s \| F'_v \tag{20}$$

$$F'^{B\times 3\times C\times \frac{H}{4}\times \frac{W}{4}}_{stacked} \rightarrow F'^{B\times \frac{H}{4}\times \frac{W}{4}\times 3\times C}_{permuted} \rightarrow F'^{B*\frac{H}{4}*\frac{W}{4}\times 3\times C}_{reshaped} \tag{21}$$

$$F^{\iota} = F'^{B*\frac{H}{4}*\frac{W}{4}\times 3\times C}_{reshaped}. \tag{22}$$

Here, $F^{\iota}$ represents the reshaped combined feature representation which is now passed to multi-head self-attention. If $$W_q^h,\ W_k^h \text{ and } W_v^h$$

represent the key, query, and value of a matrix for h as head in multi-head self-attention, then the attended feature map can be represented as:

$$F = \oiint\left( \sqsubseteq \left( \left\{ \delta\left( \frac{(F^{\iota} W_q^h)(F^{\iota} W_k^h)^T}{\sqrt{d}} \right) (F^{\iota} W_v^h) \right\}_{h=1}^{N_h} \right) W_o + F^{\iota} \right). \tag{23}$$

Here, $N_h$ represents number of heads, which is 8 and F represents the attended version of the combined feature representation, which is then reshaped, permuted and projected back to individual attended feature maps, represented as follows:

$$F'^{B*\frac{H}{4}*\frac{W}{4}\times 3\times C}_{normalized} \rightarrow F'^{B\times \frac{H}{4}\times \frac{W}{4}\times 3\times C}_{reshaped} \rightarrow F'^{B\times 3\times C\times \frac{H}{4}\times \frac{W}{4}}_{permuted} \tag{24}$$

$$F'^{B\times 3\times C\times \frac{H}{4}\times \frac{W}{4}}_{permuted} \twoheadrightarrow F_k^{B\times C\times \frac{H}{4}\times \frac{W}{4}} \because k = 1, 2, 3. \tag{25}$$

These projected feature maps are then fused together and passed through a convolutional layer to generate a unified representation, which is described as:

$$F_f = W_{1\times 1} * \ddagger\left(F_k^{B\times C\times \frac{H}{4}\times \frac{W}{4}}\right) + b_f. \tag{26}$$

Here, $F_f$ represents the final unified feature representation. A pictorial representation of the disclosed cross-region attention fusion module is shown in FIG. 3.

Figure 4:
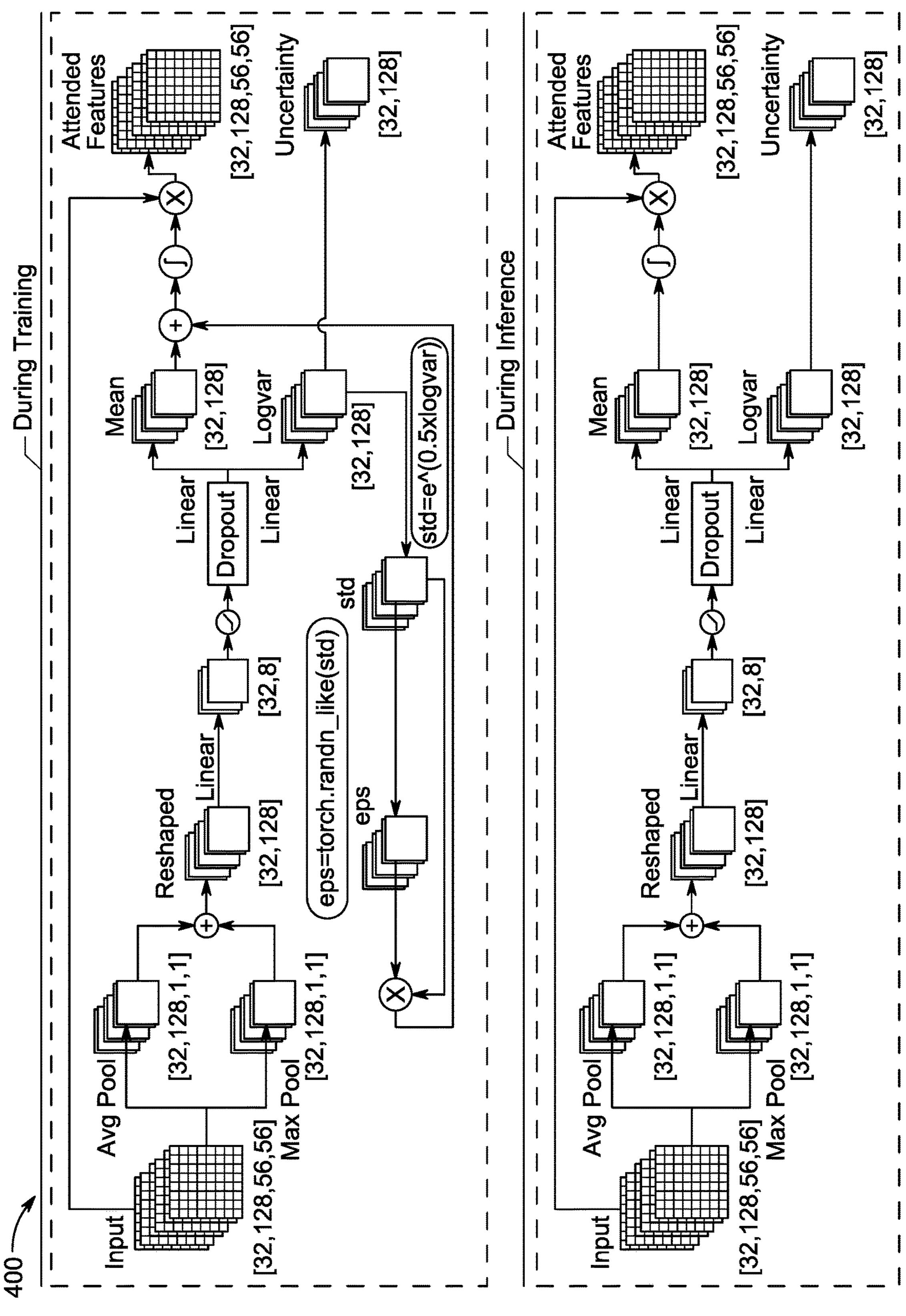
FIG. 4 depicts a block diagram of an uncertainty-guided attention module, according to certain embodiments.

FIG. 4 depicts a block diagram of an uncertainty-guided attention module, according to certain embodiments. In FIG. 4, an uncertainty-guided attention module is introduced to quantify model uncertainty by leveraging Bayesian-inspired attention weights, enabling the model to focus on informative features while providing confidence in its outputs. It is particularly relevant that, in medical imaging tasks such as tumor classification, robust handling of uncertainty is required due to data variations. The module takes as input a unified representation of the feature map produced by the cross-region attention fusion module and processes it to generate an attended feature map and an estimated uncertainty matrix, which improve feature selection by emphasizing only robust and confident features. The module begins with an input feature map, which is simultaneously passed through global average and max pooling layers to summarize spatial information into channel-wise descriptions. These descriptions are then combined to generate a single global feature representation containing both average and maximum features. Mathematically, it is represented as:

$$F_{avg} = \Cap(F_f) \tag{27}$$

$$F_{max} = \Cup(F_f) \tag{28}$$

$$F_{\circ} = F_{avg} + F_{max}. \tag{29}$$

Here, $\Cap$ represents global average pooling, $\Cup$ global max pooling, and $F_o$ represents the unified feature representation.

This unified representation is reshaped and passed to a linear layer that maps 128 channels to 8 channels, which are then processed by a ReLU activation and dropout layer to introduce non-linearity and stochasticity for uncertainty modeling. It can be defined as:

$$F'_{\circ} = \wp(\sigma(W_{\circ} \cdot F_{\circ} + b_{\circ})), \tag{30}$$

where σ represents ReLU activation, $W_o$ and $b_o$ represent the weights and bias term of the linear layer, and $F_o'$ represents the reduced feature map.

Now, two separate linear layers are applied to the reduced feature map, which restores the original number of channels, producing mean μ and log-variance λ for uncertainty, as shown in eqs. (26) and (27).

$$\mu = W_{\mu} \cdot F_{\circ} + b_{\mu} \tag{31}$$

$$\lambda = W_{\lambda} \cdot F_{\circ} + b_{\lambda} \tag{32}$$

During training, the log-variance is used to calculate the standard deviation, which is then used to generate random noise. The generated random noise is multiplied by the standard deviation and added to the mean tensor before passing through the sigmoid activation to generate attention weights.

These attention weights are then multiplied by the original input tensor to produce uncertainty-weighted attended features, whereas log-variance is returned as the uncertainty tensor. However, during inference, only the mean tensor is processed by sigmoid activation to generate attention weights; no random noise or standard deviation is added. Mathematically, this can be represented as:

$$F_w = \begin{cases} \left[\psi\left(\left(e^{0.5\lambda} \cdot \epsilon\right) + \mu\right)\right] \otimes F_f & \text{if training} \\ \psi(\mu) \otimes F_f & \text{otherwise} \end{cases}. \tag{33}$$

Here, $\epsilon \sim \mathcal{N}(0,1)$ represents random noise, $e^{0.5\lambda}$ represents standard deviation, and $F_w$ represents uncertainty guided feature map.

The final output of this module is:

$$Y_F = (F_w, \lambda). \tag{34}$$

Figure 5:
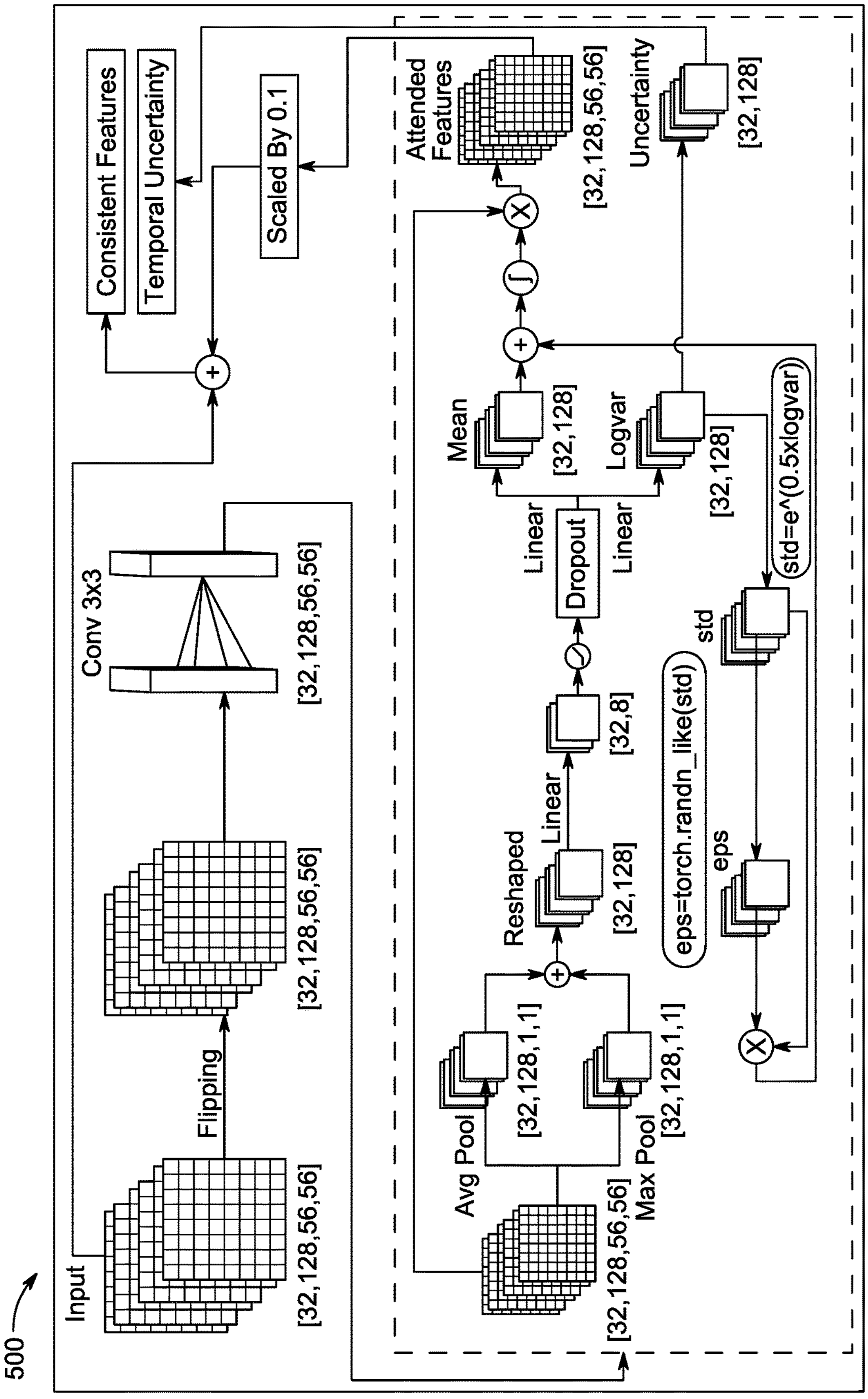
FIG. 5 depicts a block diagram of a Temporal Consistency Module, according to certain embodiments.

FIG. 5 depicts a block diagram of a temporal consistency module, according to certain embodiments. A temporal consistency module is designed to support self-supervised learning by processing augmented versions of input images during training, thereby ensuring consistent representations despite variations in input. It is designed to address spatial variations in input data arising from differences in acquisition, patient motion, or preprocessing. The module takes the attended features from the uncertainty-guided attention module as input and flips them horizontally with a 50% probability, meaning that flipping occurs only half of the time. The flipped images are then passed through a 3×3 convolutional layer to extract features, which are subsequently passed to an instance of the uncertainty-guided attention module created within the temporal consistency module. The features generated by the uncertainty-guided module are scaled by a factor of 0.1 and added to the original feature map to generate consistent features. This module ensures that only those features are passed to the classifier that receive a high confidence score, even after augmentation. In this way, the model is trained to handle spatial variations in input data. However, during inference, no augmentation is applied to the input features; instead, they are passed as is to the uncertainty-guided attention module, which further refines the feature representation. Mathematically, this can be defined as:

$$F'_w = \begin{cases} F_w + \oiiint(W_t * \gtrless(F_w) + b_T) & \text{if training} \\ F_w + \oiiint(F_w) & \text{otherwise} \end{cases}. \tag{35}$$

Here, $\oiiint$ represents the uncertainty guided attention module, $\gtrless$ represents horizontal flipping, $W_T$ and $b_T$ represent the weight and bias term of the convolutional layer, and $$Y'_F$$

represents the final consistent features.

The final output of this module is:

$$Y'_F = (F'_w, \lambda'), \tag{36}$$

where λ' is the temporal uncertainty generated by the uncertainty-guided attention module.

The consistent features produced by the temporal consistency module are passed to a feature aggregator, which consists of an adaptive average pooling layer (e.g., as illustrated in FIG. 1) that reduces the spatial dimensions to a fixed size (e.g., to a size of 7×7). This reduced feature map is passed through a 3×3 convolutional layer that increases the number of channels while preserving the spatial dimensions. After that, batch normalization is applied to stabilize the training process, followed by GELU activation to introduce non-linearity. Following that, another adaptive average pooling layer is applied, which further reduces the feature map to a fixed size of 1×1. Afterward, a flatten layer converts this feature map into a 1D vector and passes it to the classification head. In the classification head, the 1D vector is first processed by a linear layer that converts the high-dimensional feature space into a low-dimensional feature space. After that, GELU activation and a dropout layer are applied to introduce non-linearity and improve generalization. This is followed by another set of linear, GELU, and dropout layers to further reduce and refine the feature representation before it is finally passed to the last linear layer, which classifies the feature map into tumor classes.

In an embodiment, a loss function named "Composite loss" is disclosed, which is the weighted combined representation of multiple (e.g., "5") individual loss functions, namely classification loss, anatomical consistency loss, uncertainty regularization loss, cross-scale coherence loss, and temporal consistency loss.

In an embodiment, the classification loss uses a "Cross Entropy Loss" function to compute the error between actual instances and predicted instances. It directly optimizes the model to achieve accurate tumor classification. Mathematically, it can be represented as:

$$\mathcal{L}_{cls} = -\frac{1}{B}\sum_{j=1}^{B}\sum_{n=1}^{N} t_{i,n}\log(\mathcal{P}_{j,n}). \tag{37}$$

Here, B represents batch size, N represents the number of classes, $t_{j,n}$ represents the true label, $\mathcal{P}_{j,n}$ represents the predicted probability for class n, and $\mathcal{L}_{cls}$ represents the classification loss.

In an embodiment, the anatomical consistency loss ensures the spatial smoothness between anatomical regions, thereby improving the extraction of meaningful, anatomically specific features. It is achieved by applying a sigmoid activation function to anatomical masks, then calculating the difference between adjacent pixels and penalizing the model for sudden changes by averaging those differences. Mathematically, this loss function is represented as:

$$\mathcal{L}_{ant} = \frac{1}{K}\sum_{\varpi\in\{M_c,M_s,M_v\}}\left(\frac{1}{H^\circ-1}\sum_{a=1}^{H^\circ-1}\sum_{b=1}^{W^\circ}|\psi(\varpi)|_{a,b} - |\psi(\varpi)|_{a+1,b} + \frac{1}{W^\circ-1}\sum_{a=1}^{H^\circ}\sum_{b=1}^{W^\circ-1}|\psi(\varpi)|_{a,b} - |\psi(\varpi)|_{a,b+1}\right). \tag{38}$$

Here, $M_c$, $M_s$, and $M_v$ represent anatomical masks, $H^o$ and $W^o$ represent the spatial dimensions of the anatomical masks, ψ represents sigmoid activation, K represents the number of masks, which is 3, and $\mathcal{L}_{ant}$ represents anatomical consistency loss.

In an embodiment, the uncertainty regularization loss regulates uncertainties to avoid extreme high and low values, thereby improving robustness and reliability. It calculates the mean absolute deviation of log-variance from the target value (0.5) and averages across uncertainties. Mathematically, it can be represented as:

$$\mathcal{L}_\lambda = \frac{1}{\bigcup}\sum_{v=1}^{\bigcup}\frac{1}{B.C}\sum_{m=1}^{B}\sum_{n=1}^{C}|\lambda_{m,n}^{(v)} - 0.5|. \tag{39}$$

Here, U represents the number of uncertainty outputs, $\lambda^{(v)}$ represents the log-variance for uncertainty v, B represents the batch size, C represents the number of channels, and $\mathcal{L}_\lambda$ represents the uncertainty regularization loss.

In an embodiment, the cross-scale coherence loss ensures consistency between scale-specific extracted features in the multi-scale pyramid attention block, encouraging coherence in multi-scale feature representation. It is accomplished by computing the mean squared error of feature maps after downsampling them to a fixed size of 8×8 and then averaging them across scale pairs. If feature maps are less than 2, then return 0. Mathematically, this can be represented as:

$$\mathcal{L}_{COH} = \frac{1}{Q-1}\sum_{q=1}^{Q-1}\frac{1}{B\cdot C\cdot 8\cdot 8}\sum_{j=1}^{B}\sum_{c=1}^{C}\sum_{h=1}^{8}\sum_{w=1}^{8}\left(\Cap(F_q,(8,8))_{j,c,h,w} - \Cap(F_{q+1},(8,8))_{j,c,h,w}\right)^2. \quad (40)$$

Here, Q represents the number of scales, $F_q$ represents the feature map at scale q, C represents the number of channels, and $\mathcal{L}_{COH}$ represents Cross-Scale Coherence loss.

In an embodiment, the temporal consistency module ensures consistency between the original and augmented features by computing the mean squared error between them and penalizing the model for any differences (e.g., using temporal consistency loss). It improves the model's generalization by enforcing stability across both original and augmented feature representations. Mathematically, it can be defined as:

$$\mathcal{L}_{TC} = \frac{1}{B\cdot C\cdot H^{o}\cdot W^{o}}\sum_{j=1}^{B}\sum_{c=1}^{C}\sum_{h=1}^{H^{o}}\sum_{w=1}^{W^{o}}\left(F_{o_{j,c,h,w}} - F_{c_{j,c,h,w}}\right)^2. \quad (41)$$

Here, $F_o$ represents original features, $F_c$ represents consistent features, $H^o$, $W^o$ represents spatial dimensions of the feature map, and $\mathcal{L}_{TC}$ represents temporal consistency loss. In an embodiment, the composite loss function computes the overall model loss by combining the weighted representation of all these individual losses. It balances the classification accuracy with feature consistency, anatomical coherence, and regularized uncertainty. Mathematically, it can be represented as:

$$\mathcal{L}_{comp} = \mathcal{L}_{cls} + 0.1\cdot\mathcal{L}_{ant} + 0.5\cdot\mathcal{L}_{\lambda} + 0.05\cdot\mathcal{L}_{COH} + 0.1\cdot\mathcal{L}_{TC}. \quad (42)$$

Here, $\mathcal{L}_{comp}$ comp represents the composite loss. This novel loss function ensures that each part of the model's architecture contributes to the total loss of the model.

Figure 6:
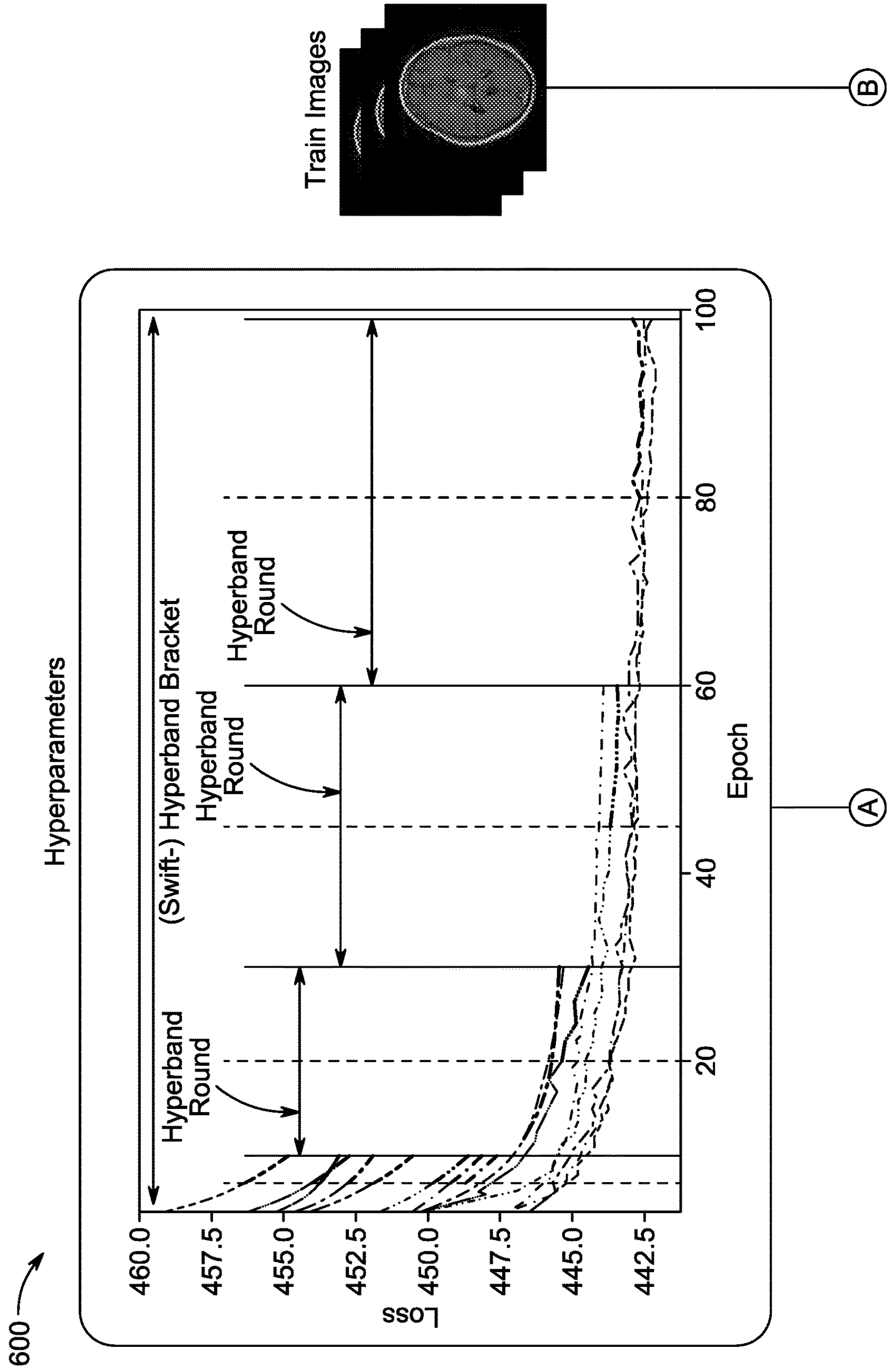
FIG. 6 depicts a methodological framework of the disclosed MAFN-APL model for brain tumor classification, according to certain embodiments.
Figure 6:
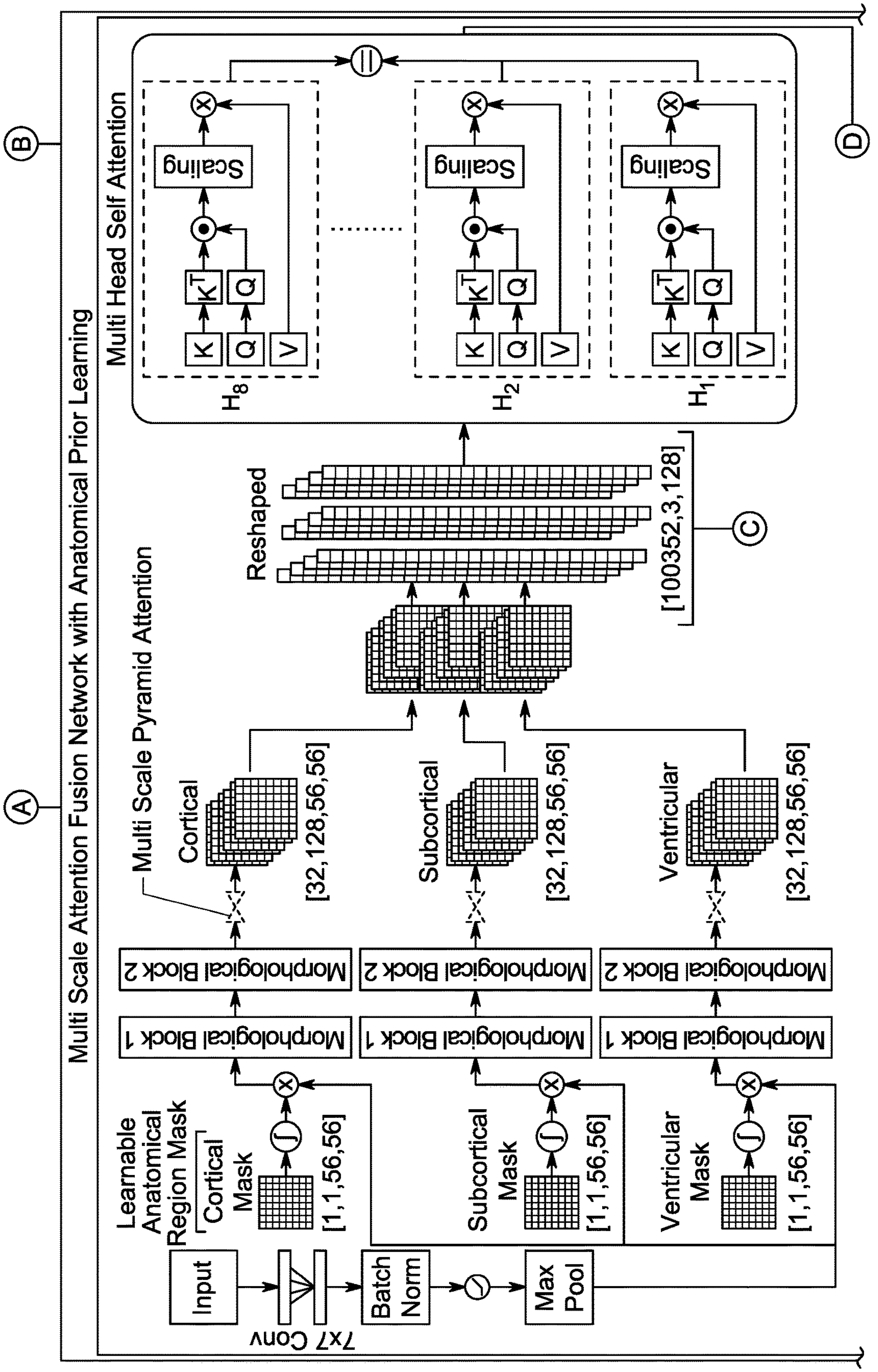
Figure 6:
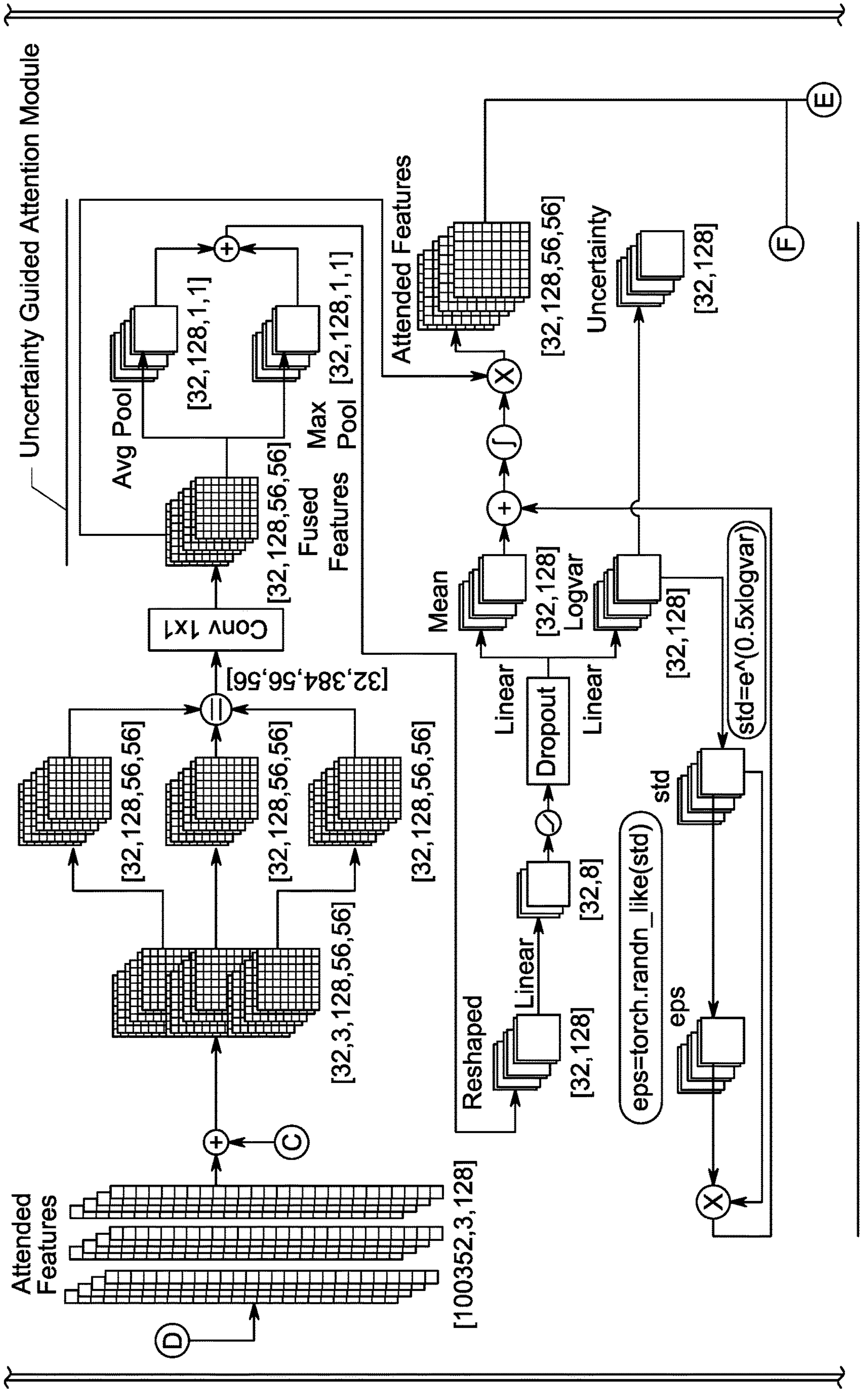
Figure 6:
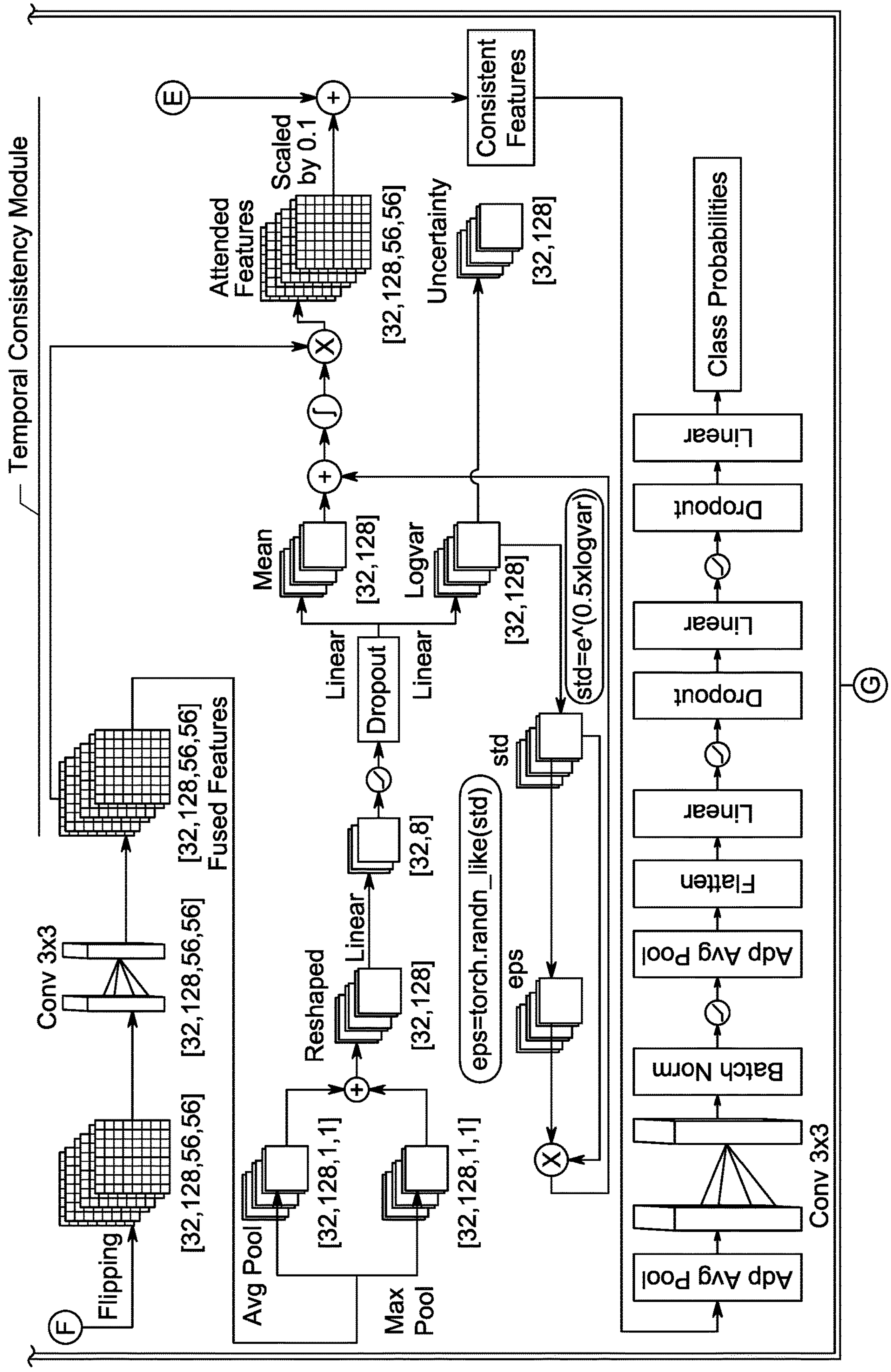
Figure 6:
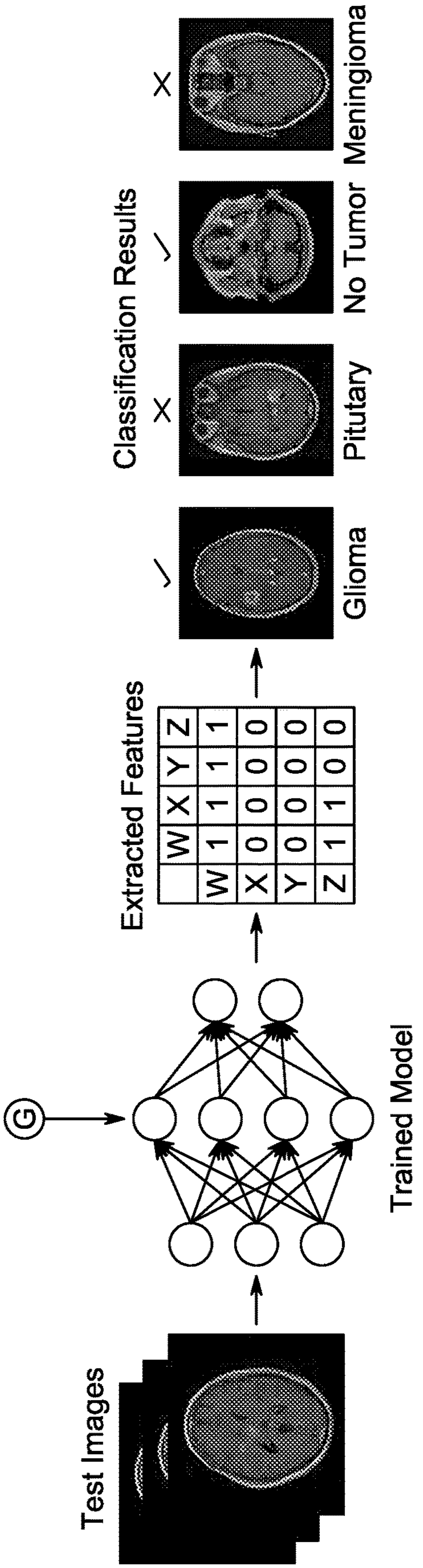

FIG. 6 depicts a methodological framework for training the MAFN-APL model for brain tumor classification, according to certain embodiments. In an embodiment, the training images are fed to the model, and the composite loss is used as the loss function. The selection of hyperparameters, such as number of epochs, optimizer, batch size, and learning rate, is done by the hyperparameter optimization technique "Hyperband Optimization" for optimal performance.

The Hyperband optimization technique is most useful when the optimal hyperparameters are to be determined in a resource-limited environment. It distributes the total budget (number of epochs) across different configurations and then continuously increases the budget for the top-performing configurations by eliminating the less-performing ones. It takes a minimum budget per bracket $\phi$ and a reduction factor $\ltimes$ as input and computes the total number of brackets and the total number of configurations per bracket using the formulas:

$$\beta_{max} = log_{\ltimes}(\phi) \quad (43)$$

$$\eta = \frac{\ltimes^{\beta}}{\beta}, \quad (44)$$

where $\beta_{max}$ represents the total number of brackets and $\eta$ represents the total number of configurations for the $\beta^{th}$ bracket.

Initially, the total budget is divided equally across all configurations, and their performance is evaluated. Those that performed well are passed to the next round, where an increased budget is allocated to them, and those that did not perform well are eliminated. After each round, the number of configurations is reduced by the factor of $\ltimes$ and the process continues till only one configuration remains. This hyperparameter configuration is then used to train the model.

In this example, the minimum budget per bracket was 30 (epochs), and the reduction factor was considered as 3. With this setup, the selected hyperparameter configuration by hyperband optimization is shown in Table 1 below.

TABLE 1

Given hyperparameter range and selected hyperparameter configuration

| Hyperparameter | Given Range | Selected Configuration |
|---|---|---|
| Epochs | 50-150 | 100 |
| Batch size | 16, 32, 64, 128, 512 | 512 |
| Learning rate | 0.0001-0.01 | 0.001 |
| Optimizer | Adam, SGD, AdamW | AdamW |
| Weight decay | 0.1-0.001 | 0.01 |

In an embodiment, the test images are fed into the disclosed model, and its performance is evaluated using various evaluation metrics. To analyze the classification performance, evaluation metrics including accuracy, precision, recall, and F1-score are used. To analyze the computational complexity of the model, GMACs, the total number of parameters, inference time, memory usage, and energy consumption are considered. Various ablation studies are also conducted to analyze the impact of individual components on overall performance.

Figure 7:
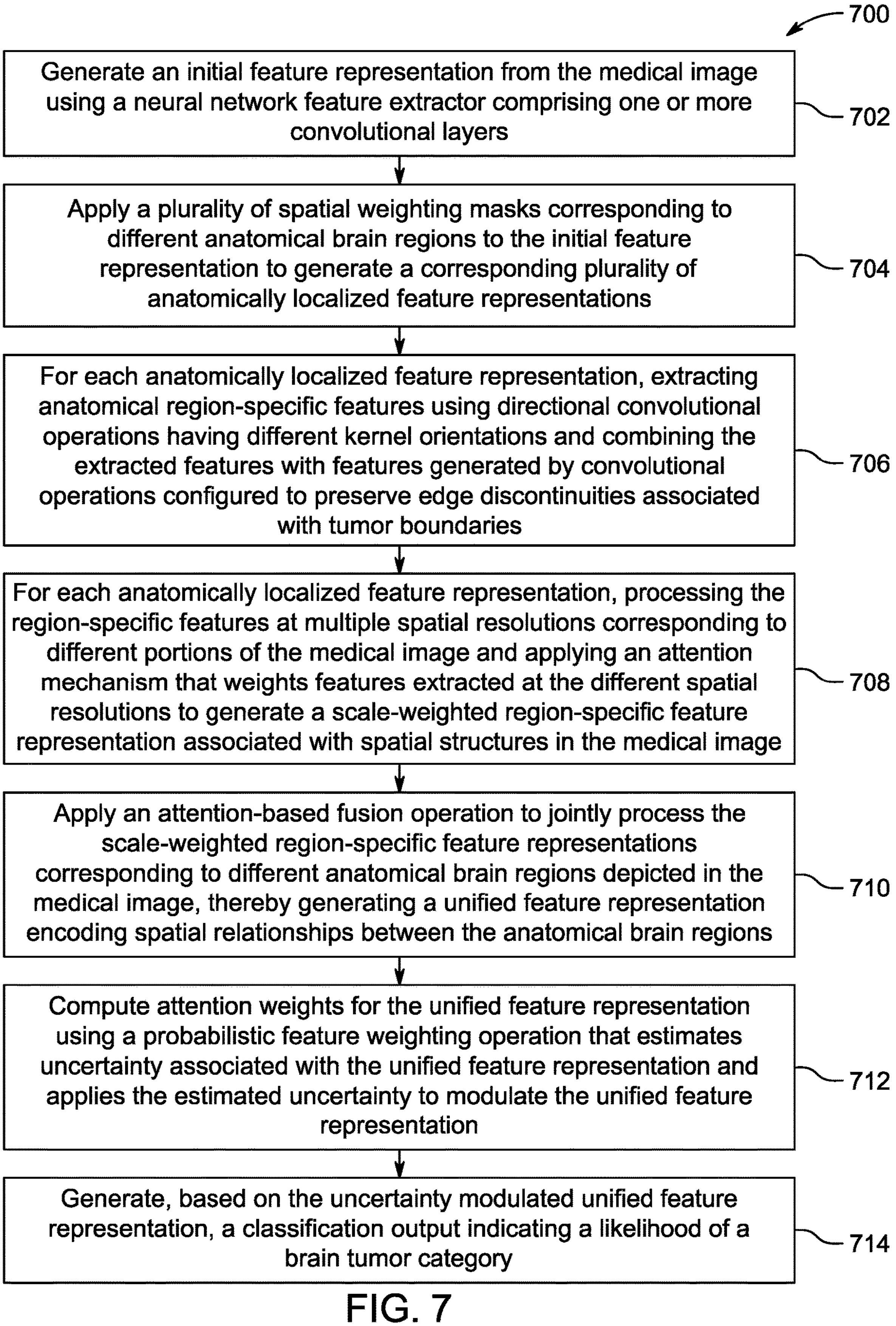
FIG. 7 depicts a flow diagram of a method for brain tumor detection and classification, according to certain embodiments.

FIG. 7 is a flow diagram of a method for brain tumor detection and classification, according to certain embodiments.

At step 702, an initial feature representation is generated from a medical image of a brain using a neural network feature extractor comprising one or more convolutional layers. The process begins by feeding the medical image into a neural network feature extractor, which includes one or more convolutional layers configured to process raw pixel data into a high-dimensional feature map. This feature map retains spatial information and highlights salient visual attributes relevant for subsequent processing. In some embodiments, the convolutional layers may be jointly optimized with downstream components of the neural network during training to facilitate end-to-end feature learning. Convolutional operations enable extraction of texture, contrast, and morphological details across the medical image at multiple scales.

At step 704, a plurality of spatial weighting masks corresponding to different anatomical brain regions are applied to the initial feature representation to generate a plurality of anatomically localized feature representations. The spatial weighting masks selectively emphasize feature activations corresponding to different anatomical regions of the brain. In some embodiments, the spatial weighting masks comprise learnable parameters that are jointly optimized with parameters of the neural network, without requiring externally generated anatomical segmentations. By applying these masks to the initial feature representation, anatomically localized feature representations are generated, each corresponding to a different brain region, thereby enabling region-specific analysis while reducing interference from unrelated regions.

At step 706, for each anatomically localized feature representation, anatomical region-specific features are extracted using directional convolutional operations having different kernel orientations, and the extracted features are combined with features generated by convolutional operations configured to preserve edge discontinuities associated with tumor boundaries. Directional convolutional operations use convolutional kernels oriented along multiple angular directions (e.g., horizontal, vertical, or oblique orientations) to capture orientation specific feature patterns within anatomical regions. These operations facilitate detection of anisotropic structures, such as interfaces or tumor infiltrative margins. The extracted features are further combined with features generated by convolutional operations configured to preserve edge discontinuities, enabling retention of sharp transitions corresponding to tumor boundaries, cystic regions, and other clinically significant or relevant structures in neuro-oncology imaging.

At step 708, for each anatomically localized feature representation, the region-specific features are processed at multiple spatial resolutions corresponding to different portions of the medical image, and an attention mechanism is applied to weight features extracted at the different spatial resolutions to generate a scale-weighted region-specific feature representation. Multiscale or multiresolution processing may include downsampling the region-specific features to a plurality of reduced spatial resolutions, applying convolutional operations at each reduced spatial resolution, and upsampling outputs of the convolutional operations to a common spatial resolution prior to applying the attention mechanism. The attention mechanism computes weighting coefficients across the multiple resolutions, which may be normalized across the resolutions, to emphasize diagnostically relevant features at different scales. This results in a scale-weighted, region-specific feature representation that captures both fine-grained and coarse anatomical details.

At step 710, an attention-based fusion operation is performed to jointly process the scale-weighted region-specific feature representations corresponding to different anatomical brain regions, thereby generating a unified feature representation encoding spatial relationships between the anatomical brain regions. The fusion operation may include applying a self-attention mechanism across the anatomically localized feature representations to generate the unified feature representation. This operation enables representation of interactions between different anatomical brain regions at corresponding spatial locations, thereby capturing inter-region dependencies and spatial relationships, such as adjacency, symmetry, or patterns of pathological spread, relevant for brain tumor characterization.

At step 712, attention weights are computed for the unified feature representation using a probabilistic feature weighting operation that estimates uncertainty associated with the unified feature representation and applies the estimated uncertainty to modulate the unified feature representation. The probabilistic feature weighting operation may compute channel-wise attention weights by estimating uncertainty values for feature channels and adjusting the feature representation based on the estimated uncertainty. Such estimation might be achieved using Bayesian neural networks, Monte Carlo dropout, or similar approaches that provide measures of epistemic (model) and/or aleatoric (data) uncertainty. During training, stochastic attention weights may be generated by estimating uncertainty values and injecting noise scaled by the estimated uncertainty prior to computing attention weights. The calculated uncertainty values are used to modulate the unified feature representation, attenuating features with high uncertainty or amplifying those with low uncertainty, thereby enhancing the reliability of features used in the final prediction. Accordingly, this uncertainty-guided attention operation enables the system to account for uncertainty in feature representations and adjust feature contributions accordingly.

At step 714, a classification output is generated based on the uncertainty-modulated unified feature representation, the output indicating the likelihood of a brain tumor category. The classification may be performed using one or more neural network layers configured to map the unified feature representation to class likelihood values corresponding to different brain tumor categories. The output indicates the likelihood of the medical image belonging to one or more brain tumor categories, such as glioblastoma, meningioma, metastasis, or unremarkable (non-tumorous) tissue. In some embodiments, the output may also include associated confidence scores, thereby providing actionable diagnostic information for clinical decision-making while indicating the system's certainty in its assessment. The method 700, therefore, describes a tightly integrated pipeline leveraging anatomical knowledge, multiscale analysis, attention mechanisms, uncertainty quantification, and machine learning-driven classification to achieve robust, interpretable, and clinically relevant brain tumor detection from medical images.

In some embodiments, training of the neural network model (e.g., MAFN-APL model 100) further includes a temporal consistency module configured to process the unified feature representation and an augmented feature representation generated by applying a spatial augmentation (e.g., horizontal flipping) to the unified feature representation. The temporal consistency module generates corresponding consistency constrained feature representations, and parameters of the neural network are updated based on differences between the consistency constrained feature representations. In some embodiments, the temporal consistency module further comprises applying an instance of the probabilistic feature weighting operation to the augmented feature representation prior to generating the consistency constrained feature representations. During inference, the spatial augmentation and generation of the augmented feature representation are disabled.

In some embodiments, updating parameters of the neural network includes optimizing a composite loss function comprising a classification loss, an anatomical consistency loss based on spatial differences between the spatial weighting masks, an uncertainty regularization loss based on uncertainty values associated with feature channels, a cross-scale coherence loss based on differences between feature representations at different spatial resolutions, and a temporal consistency loss based on differences between the unified feature representation and the augmented feature representation.

Figure 8:
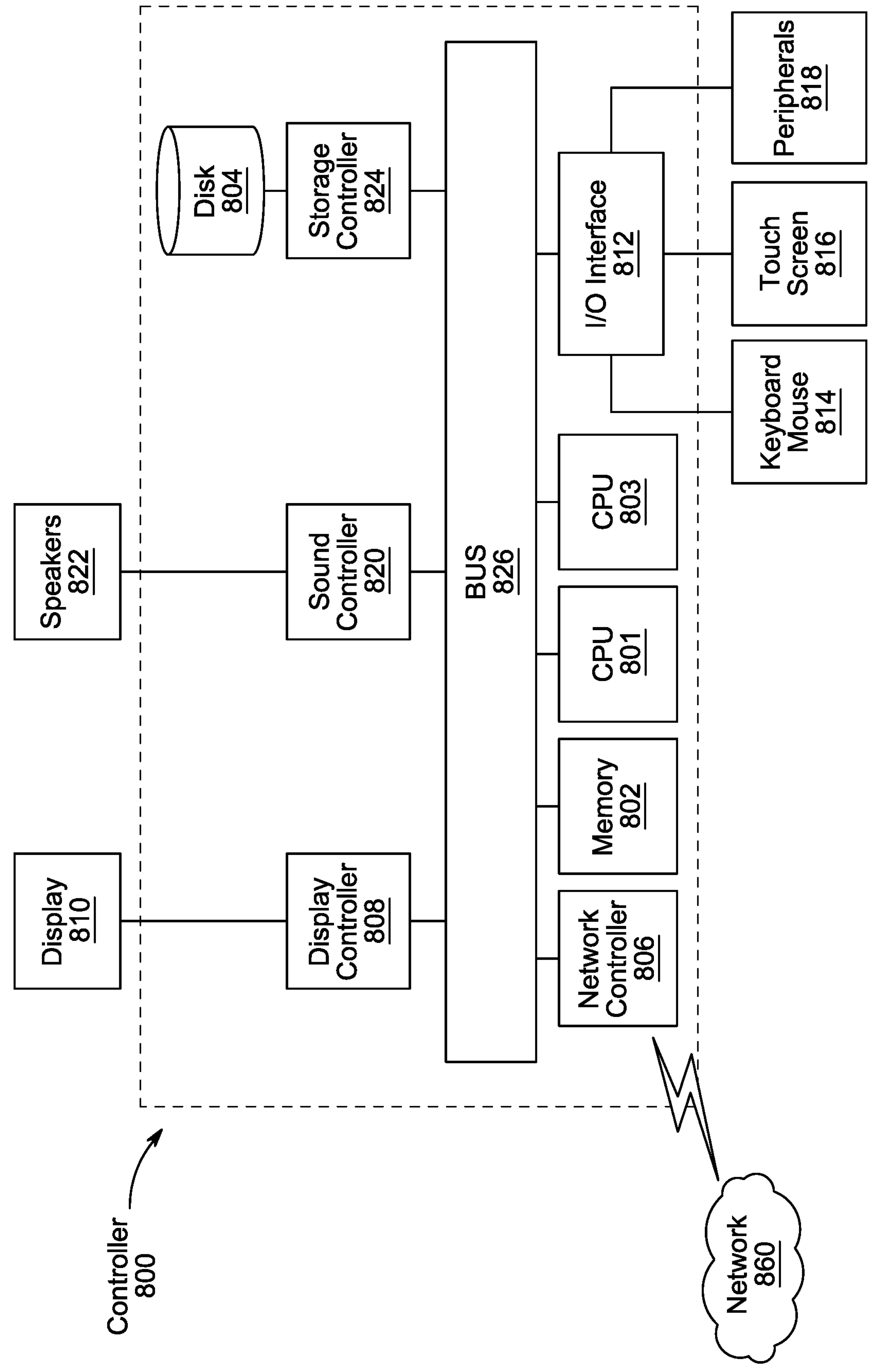
FIG. 8 is an illustration of a non-limiting example of details of computing hardware used in the computing system, according to certain embodiments.

The computing device in FIG. 8 also includes a network controller 806, such as an Intel Ethernet PRO network interface card from Intel Corporation of America, for interfacing with network 860. As can be appreciated, the network 860 can be a public network, such as the Internet, or a private network such as an LAN or WAN network, or any combination thereof and can also include PSTN or ISDN subnetworks. The network 860 can also be wired, such as an Ethernet network, or can be wireless such as a cellular network including EDGE, 3G, 4G, and 5G wireless cellular systems. The wireless network can also be WiFi, Bluetooth, or any other wireless form of communication that is known.

The computing device further includes a display controller 808, such as a NVIDIA GeForce GTX or Quadro graphics adaptor from NVIDIA Corporation of America for interfacing with display 810, such as a Hewlett Packard HPL2445w LCD monitor. A general purpose I/O interface 812 interfaces with a keyboard and/or mouse 814 as well as a touch screen panel 816 on or separate from display 810. General purpose I/O interface also connects to a variety of peripherals 818 including printers and scanners, such as an OfficeJet or DeskJet from Hewlett Packard.

A sound controller 820 is also provided in the computing device such as Sound Blaster X-Fi Titanium from Creative, to interface with speakers/microphone 822 thereby providing sounds and/or music.

The general purpose storage controller 824 connects the storage medium disk 804 with communication bus 826, which may be an ISA, EISA, VESA, PCI, or similar, for interconnecting all of the components of the computing device. A description of the general features and functionality of the display 810, keyboard and/or mouse 414, as well as the display controller 808, storage controller 824, network controller 806, sound controller 820, and general purpose I/O interface 812 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 9.

Figure 9:
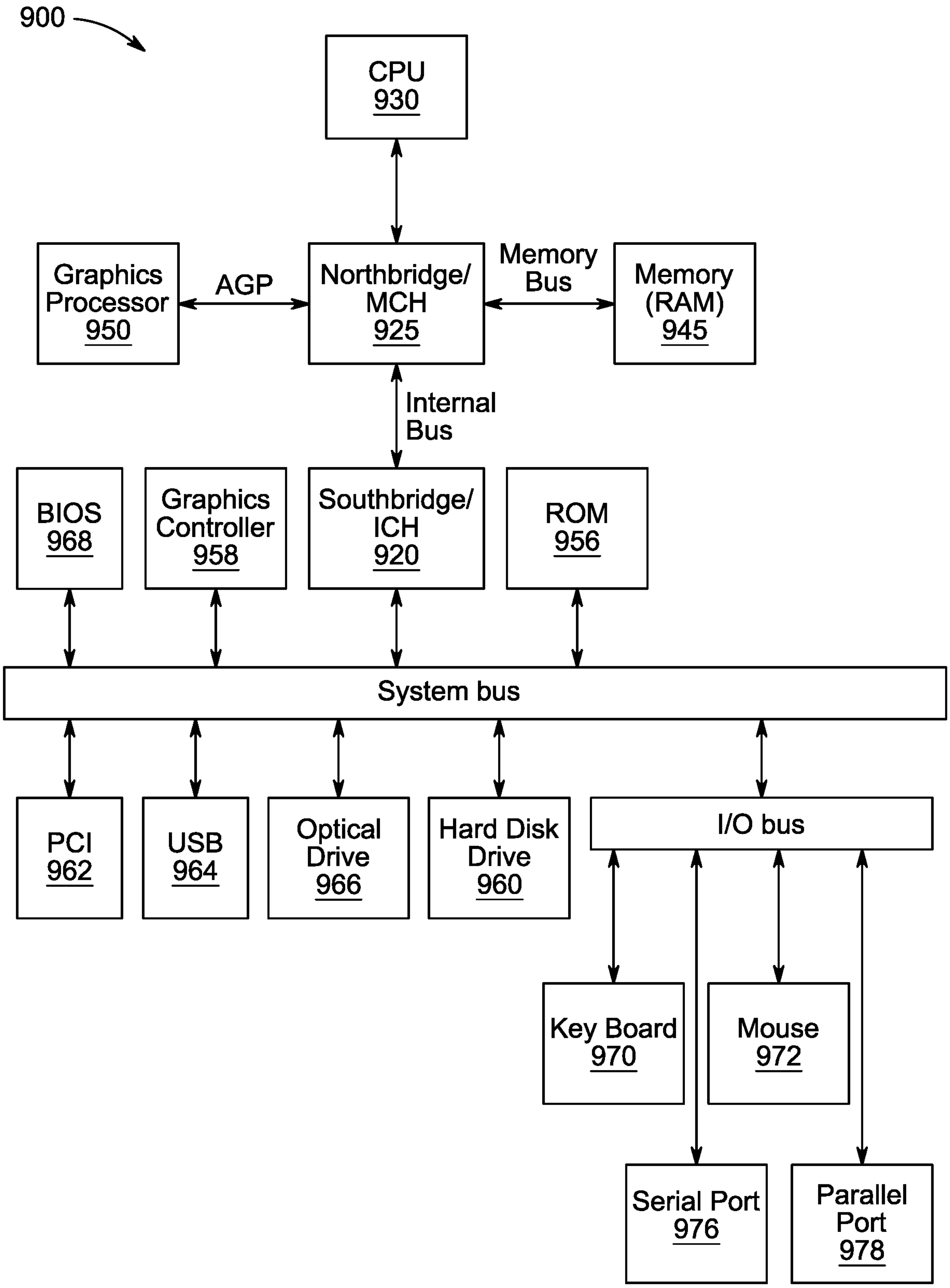
FIG. 9 is an exemplary schematic diagram of a data processing system used within the computing system, according to certain embodiments.

FIG. 9 shows a schematic diagram of a data processing system 900, according to certain embodiments, for performing the functions of the exemplary embodiments. The data processing system 900 is an example of a computer in which code or instructions implementing the processes of the illustrative embodiments may be located.

In FIG. 9, data processing system 900 employs a hub architecture including a north bridge and memory controller hub (NB/MCH) 925 and a south bridge and input/output (I/O) controller hub (SB/ICH) 920. The central processing unit (CPU) 530 is connected to NB/MCH 925. The NB/MCH 925 also connects to the memory 545 via a memory bus, and connects to the graphics processor 950 via an accelerated graphics port (AGP). The NB/MCH 925 also connects to the SB/ICH 920 via an internal bus (e.g., a unified media interface or a direct media interface). The CPU Processing unit 930 may contain one or more processors and even may be implemented using one or more heterogeneous processor systems.

Figure 10:
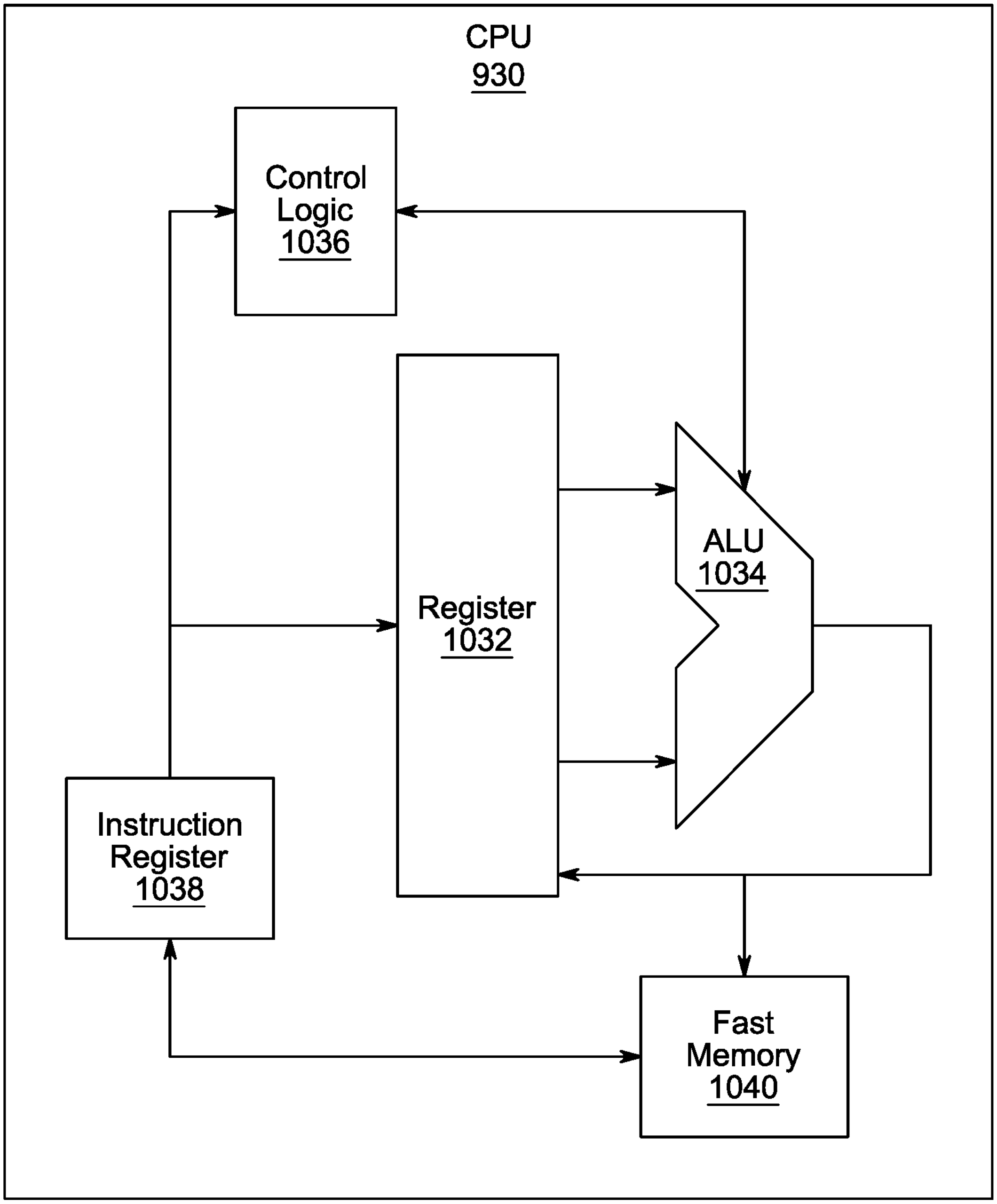
FIG. 10 is an exemplary schematic diagram of a processor used with the computing system, according to certain embodiments.

For example, FIG. 10 shows one implementation of CPU 930. In one implementation, the instruction register 938 retrieves instructions from the fast memory 940. At least part of these instructions are fetched from the instruction register 1038 by the control logic 636 and interpreted according to the instruction set architecture of the CPU 930. Part of the instructions can also be directed to the register 1032. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 1034 that loads values from the register 1032 and performs logical and mathematical operations on the loaded values according to the instructions. The results from these operations can be feedback into the register and/or stored in the fast memory 940. According to certain implementations, the instruction set architecture of the CPU 930 can use a reduced instruction set architecture, a complex instruction set architecture, a vector processor architecture, a very large instruction word architecture. Furthermore, the CPU 930 can be based on the Von Neuman model or the Harvard model. The CPU 930 can be a digital signal processor, an FPGA, an ASIC, a PLA, a PLD, or a CPLD. Further, the CPU 930 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 9, the data processing system 900 can include that the SB/ICH 920 is coupled through a system bus to an I/O Bus, a read only memory (ROM) 956, universal serial bus (USB) port 964, a flash binary input/output system (BIOS) 968, and a graphics controller 958. PCI/PCIe devices can also be coupled to SB/ICH 988 through a PCI bus 962.

The PCI devices may include, for example, Ethernet adapters, add-in cards, and PC cards for notebook computers. The Hard disk drive 960 and CD-ROM 966 can use, for example, an integrated drive electronics (IDE) or serial advanced technology attachment (SATA) interface. In one implementation the I/O bus can include a super I/O (SIO) device.

Further, the hard disk drive (HDD) 960 and optical drive 966 can also be coupled to the SB/ICH 920 through a system bus. In one implementation, a keyboard 970, a mouse 972, a parallel port 978, and a serial port 976 can be connected to the system bus through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 11:
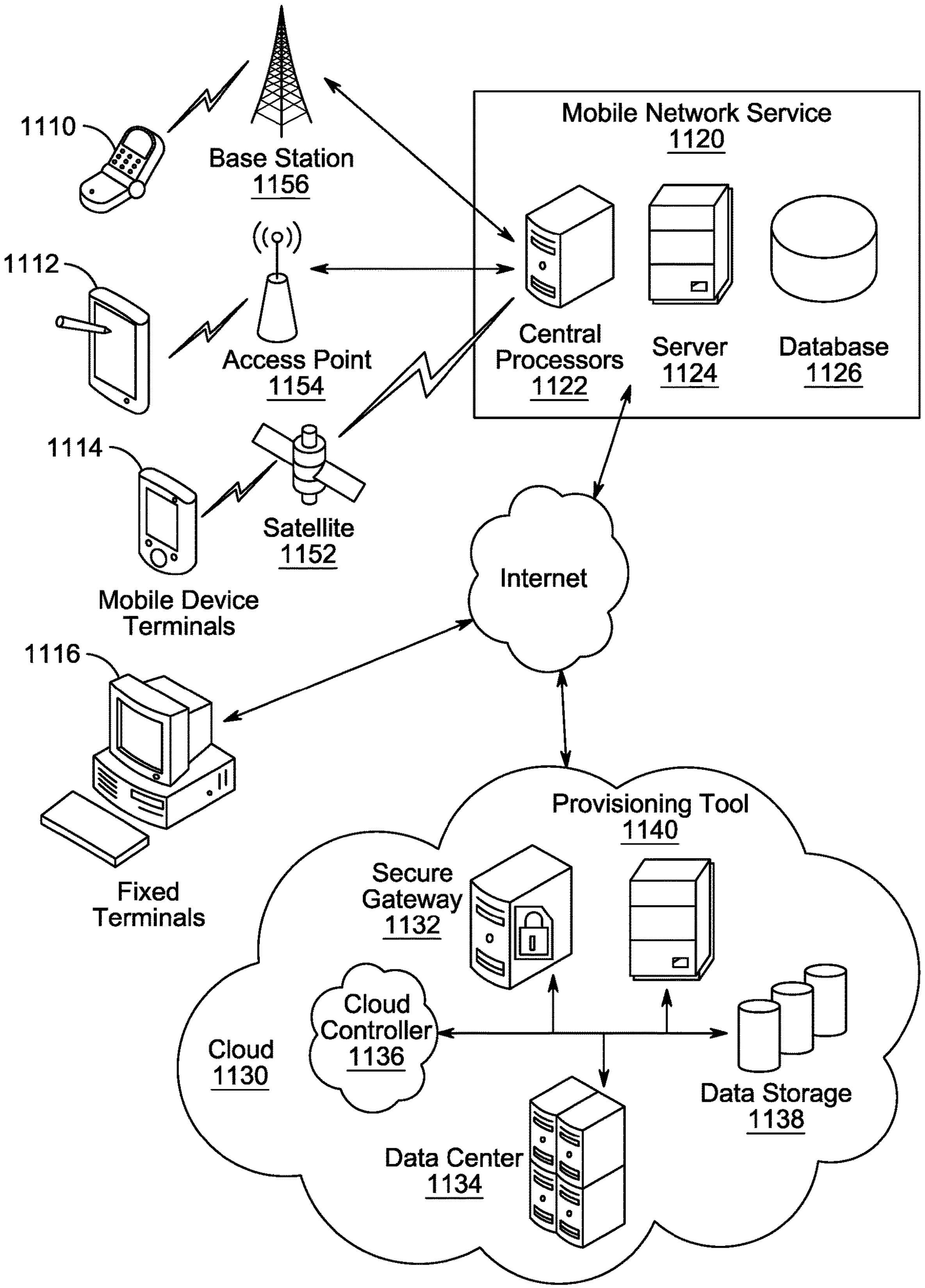
FIG. 11 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 11, in addition to various human interface and communication devices (e.g., display monitors, smart phones, tablets, personal digital assistants (PDAs)). More specifically, FIG. 11 illustrates client devices including a smart phone 1111, a tablet 1112, a mobile device terminal 1114 and fixed terminals 1116. These client devices may be commutatively coupled with a mobile network service 1120 via a base station 1156, an access point 1154, a satellite 1152 or via an internet connection. The mobile network service 1120 may comprise central processors 1122, a server 1124 and a database 1126. The fixed terminals 1116 and the mobile network service 1120 may be commutatively coupled via an internet connection to functions in cloud 1130 that may comprise a security gateway 1132, a data center 1134, a cloud controller 1136, a data storage 1138 and a provisioning tool 1140. The network may be a private network, such as the LAN or the WAN, or may be the public network, such as the Internet. Input to the system may be received via direct user input and received remotely either in real-time or as a batch process. Additionally, some implementations may be performed on modules or hardware not identical to those described. Accordingly, other implementations are within the scope that may be disclosed.

The above-described hardware description is a non-limiting example of corresponding structure for performing the functionality described herein.

Numerous modifications and variations of the present disclosure are possible in light of the above teachings. It is therefore to be understood that the invention may be practiced otherwise than as specifically described herein.

The invention claimed is:

1. A computer-implemented method for analyzing a medical image of a brain using a trained neural network, the method comprising:

generating an initial feature representation from the medical image using a neural network feature extractor comprising one or more convolutional layers;

applying a plurality of spatial weighting masks corresponding to different anatomical brain regions to the initial feature representation to generate a corresponding plurality of anatomically localized feature representations;

for each anatomically localized feature representation, extracting anatomical region-specific features using directional convolutional operations having different kernel orientations and combining the extracted features with features generated by convolutional operations configured to preserve edge discontinuities associated with tumor boundaries;

for each anatomically localized feature representation, processing the region-specific features at multiple spatial resolutions corresponding to different portions of the medical image and applying an attention mechanism that weights features extracted at the different spatial resolutions to generate a scale-weighted region-specific feature representation associated with spatial structures in the medical image;

applying an attention-based fusion operation to jointly process the scale-weighted region-specific feature representations corresponding to different anatomical brain regions depicted in the medical image, thereby generating a unified feature representation encoding spatial relationships between the anatomical brain regions;

computing attention weights for the unified feature representation using a probabilistic feature weighting operation that estimates uncertainty associated with the unified feature representation and applies the estimated uncertainty to modulate the unified feature representation; and generating, based on the uncertainty modulated unified feature representation, a classification output indicating a likelihood of a brain tumor category.

2. The method of claim 1, wherein the plurality of spatial weighting masks includes learnable parameters jointly optimized with parameters of the neural network, and no externally generated anatomical segmentation is used to define the spatial weighting masks.

3. The method of claim 1, wherein processing the anatomical region-specific features at multiple spatial resolutions includes:

downsampling the anatomical region-specific features to a plurality of reduced spatial resolutions, applying convolutional operations at each reduced spatial resolution, and upsampling outputs of the convolutional operations to a common spatial resolution prior to applying the attention mechanism.

4. The method of claim 1, wherein the attention-based fusion operation includes:

applying a self-attention mechanism across the anatomically localized feature representations to generate the unified feature representation encoding interactions between different anatomical brain regions at corresponding spatial locations.

5. The method of claim 1 further comprising:

training the neural network, wherein training comprises:

generating stochastic attention weights in the probabilistic feature weighting operation by (a) estimating an uncertainty value for feature channels, and (b) injecting noise scaled by the estimated uncertainty value prior to computing attention weights.

6. The method of claim 1 further comprising:

training the neural network, wherein training comprises:

processing, by a temporal consistency module, the unified feature representation and an augmented feature representation to generate corresponding consistency constrained feature representations, wherein the augmented feature representation is generated by applying a spatial augmentation to the unified feature representation, and updating parameters of the neural network based on differences between the consistency constrained feature representations.

7. The method of claim 6, wherein updating parameters of the neural network includes:

optimizing a composite loss function including:

(i) a classification loss based on the classification output, (ii) an anatomical consistency loss based on spatial differences between the plurality of spatial weighting masks, (iii) an uncertainty regularization loss based on uncertainty values associated with feature channels, (iv) a cross-scale coherence loss based on differences between feature representations at different spatial resolutions, and (v) a temporal consistency loss based on differences between the unified feature representation and the augmented feature representation.

8. The method of claim 6, wherein, during an inference phase, the spatial augmentation and generation of the augmented feature representation are disabled.

9. The method of claim 6, wherein the temporal consistency module comprises applying an instance of the probabilistic feature weighting operation to the augmented feature representation prior to generating the consistency constrained feature representations.

10. The method of claim 1, wherein the directional convolutional operations include convolutional kernels oriented along at least two different angular directions to capture orientation-specific feature patterns within the anatomical brain regions.

11. The method of claim 1, wherein the attention mechanism that weights features extracted at the different spatial resolutions computes normalized weighting coefficients across the multiple spatial resolutions prior to generating the scale-weighted region-specific feature representation.

12. A system for analyzing a medical image of a brain, the system comprising:

one or more processors; and a memory storing instructions that, when executed by the one or more processors, cause the one or more processors to:

generate an initial feature representation from the medical image using a neural network feature extractor;

apply a plurality of spatial weighting masks corresponding to different anatomical brain regions to the initial feature representation to generate a plurality of anatomically localized feature representations;

apply directional convolutional operations to the anatomically localized feature representations to generate anatomical region-specific features;

apply attention mechanisms to the anatomical region-specific features to weight features across multiple spatial resolutions and across the anatomical brain regions, thereby generating a unified feature representation encoding spatial relationships between the anatomical brain regions;

determine uncertainty associated with the unified feature representation and adjust the unified feature representation based on the determined uncertainty; and generate, based on the adjusted unified feature representation, an output indicating a likelihood of a brain tumor category.

13. The system of claim 12, wherein the plurality of spatial weighting masks include learnable parameters jointly optimized with parameters of the neural network, and no externally generated anatomical segmentation is used to define the spatial weighting masks.

14. The system of claim 12, wherein the one or more processors are further configured to:

process the anatomical region-specific features at multiple spatial resolutions by:

downsampling the anatomical region-specific features to a plurality of reduced spatial resolutions, applying convolutional operations at each reduced spatial resolution, and upsampling outputs of the convolutional operations to a common spatial resolution prior to applying the attention mechanisms.

15. The system of claim 12, wherein the attention mechanisms include a self-attention mechanism applied across the anatomically localized feature representations to generate a fused feature representation encoding interactions between different anatomical brain regions at corresponding spatial locations.

16. The system of claim 12, wherein the memory further stores instructions that, when executed by the one or more processors during training of the neural network, cause the one or more processors to:

generate stochastic attention weights by determining an uncertainty value for feature channels and injecting noise scaled by the determined uncertainty value prior to adjusting the unified feature representation.

17. The system of claim 12, wherein the memory further stores instructions that, when executed by the one or more processors during training of the neural network, cause the one or more processors to:

apply a spatial augmentation to the unified feature representation to generate an augmented feature representation;

apply an instance of the probabilistic feature weighting operation to the augmented feature representation; and update parameters of the neural network based on differences between the unified feature representation and the augmented feature representation.

18. A non-transitory computer-readable medium storing instructions that, when executed by one or more processors, cause the one or more processors to:

generate an initial feature representation from a medical image of a brain using a neural network feature extractor;

apply a plurality of spatial weighting masks corresponding to different anatomical brain regions to the initial feature representation to generate a plurality of anatomically localized feature representations;

apply directional convolutional operations to the anatomically localized feature representations to generate anatomical region-specific features;

apply attention mechanisms to the anatomical region-specific features to weight features across multiple spatial resolutions and across the anatomical brain regions, thereby generating a unified feature representation encoding spatial relationships between the anatomical brain regions;

determine uncertainty associated with the unified feature representation and adjust the unified feature representation based on the determined uncertainty; and generate, based on the adjusted unified feature representation, an output indicating a likelihood of a brain tumor category.

19. The non-transitory computer-readable medium of claim 18, wherein the instructions further cause the one or more processors, during training of the neural network, to:

generate stochastic attention weights by estimating an uncertainty value for feature channels and injecting noise scaled by the estimated uncertainty value prior to adjusting the unified feature representation.

20. The non-transitory computer-readable medium of claim 18, wherein the instructions further cause the one or more processors, during training of the neural network, to:

apply a spatial augmentation to the unified feature representation to generate an augmented feature representation;

apply an instance of the probabilistic feature weighting operation to the augmented feature representation; and update parameters of the neural network based on differences between the unified feature representation and the augmented feature representation.

* * * * *